United States Patent
Wittwer et al.

(10) Patent No.: US 6,472,156 B1
(45) Date of Patent: Oct. 29, 2002

(54) HOMOGENEOUS MULTIPLEX HYBRIDIZATION ANALYSIS BY COLOR AND TM

(75) Inventors: Carl T. Wittwer, Salt Lake City, UT (US); Mark G. Herrmann, Salt Lake City, UT (US)

(73) Assignee: The University of Utah, Salt Lake City, UT (US)

( * ) Notice: Subject to any disclaimer, the term of this patent is extended or adjusted under 35 U.S.C. 154(b) by 0 days.

(21) Appl. No.: 09/651,374

(22) Filed: Aug. 30, 2000

Related U.S. Application Data

(60) Provisional application No. 60/151,494, filed on Aug. 30, 1999.

(51) Int. Cl.[7] .......................... C12Q 1/68; C12P 19/34; G01N 33/00; C07H 21/00
(52) U.S. Cl. .......................... 435/6; 435/91.2; 436/94; 536/25.32
(58) Field of Search ...................... 435/6, 91.2; 436/94; 536/25.32

(56) References Cited

U.S. PATENT DOCUMENTS

| | | |
|---|---|---|
| 5,455,175 A | 10/1995 | Wittwer et al. |
| 6,197,520 B1 | 3/2001 | Wittwer et al. |

OTHER PUBLICATIONS

Bagwell CB, Adams EG. Fluorescence spectral overlap compension for any number of flow cytometry parameters. Ann N Y Acad Sci. 1993 Mar. 20;677:167–84.

Bernard PS, Lay MJ, Wittmer CT. Integrated amplification and detection of the C677T point mutation in the methylenetetrahydrofolate reductase gene by fluorescence resonance energy transfer and probe melting curves. Anal Biochem, 1998 Jan. 1;255(1):101–7.

Bernard PS, Ajioka RS, Kushar JP. Wittwer CT. Homogeneous multiplex genotyping of hemochromatosis mutations with fluroescent hybridization probes. Am J Pathol. 1998 Oct; 153(4):1055–61.

Bernard PS, Pritham GH, Wittwer CT. Color multiplexing hybridization probes using the apolipprotein E locus as a model system for genotyping. Anal Biochem. 1999 Sep. 10;273(2):221–8.

Brown T, Leonard GA, Booth ED, Kneale G.Influence of pH on the conformation and stability of mismatch base–pairs in DNA. J Mol Biol. 1990 Apr. 5;212(3):437–40. Review.

(List continued on next page.)

Primary Examiner—Gary Benzion
Assistant Examiner—J. Tung
(74) Attorney, Agent, or Firm—Dorsey & Whitney LLP; Richard F. Trecartin

(57) ABSTRACT

The invention provides methods and devices for analyzing sequence variations in nucleic acid samples comprising multiple loci, each having two, three or more possible allelic sequences. The method involves combining at least a first and second pair of oligonucleotide probes with the nucleic acid sample. The first pair of probes is capable of hybridizing in proximity to each other within a segment of the nucleic acid sample comprising the first locus and the second pair is capable of hybridizing in proximity to each other within a segment of the nucleic acid sample comprising the second locus. The first member of each probe pair comprises a FRET donor and the second member comprises a FRET acceptor, the FRET acceptor of the first probe pair member having a different emission spectrum from the FRET acceptor of the second probe pair. Upon hybridization, the proximity of the first and second member of each probe pair is sufficient to allow fluorescence resonance energy transfer between the FRET donor and the FRET acceptor.

11 Claims, 22 Drawing Sheets

OTHER PUBLICATIONS

Gaffney BL, Jones RA, Thermodynamic comparison of the base pairs formed by the carcinogenic lesion O6–methylguanine with reference both to Watson–Crick pairs and to mismatched pairs. Biochemistry. 1989 Jul. 11;28(14):5881–9.

Guo Z, Liu Q, Smith LM. Enhanced discrimination of single nucleotide polymorphisms by artificial mismatch hybridization. Nat Biotechnol. 1997 Apr.; 15(4):331–5.

Lay MJ, Wittmer CR Real–time fluroescence genotyping of factor V Leiden during rapid–cycle PCR, Clin Chem. 1997 Dec.;43(12):2262–7. temperature.

Lee LG, Livak KJ, Mullah B, Graham RJ, Vinayak RS, Woudenberg TM, Seven–color, homogeneous detection of six PCR products. Biotechniques. 1999 Aug.; 27(2):342–9.

Livak KJ, Flood SJ, Mararo J, Giusti W, Deetz K. Oligonucleotides with fluorescent dyes at opposite ends provide a quenched probe system useful for detecting PCR product and nucleic acid hybridization. PCR Methods Appl. 1995 Jun.;4(6):357–62.

Lyon E, Milson A, Phan T, Wittwer CT. Detection and Identification of Base Alterations Within the Regions of Factor V Leiden by Fluorescent Melting Curves. Mol Diagn. 1998 Dec.; 3(4):203–209.

Marras SA, Kramer FR, Tyagi S. Multiplex detection of single–nucleotide variations using molecular beacons. Genet Anal. 1999 Feb.; 14(5–6):151–6.

Morrison TB, Weis JJ, Wittwer CT. Quantification of low–copy transcripts by continuous SYBR Green I monitoring during amplification. Biotechniques. 1998 Jun.;24(6):954–8, 960, 962.

Nazarenko IA, Bhatnagar SK, Hohman RJ. A closed tube format for amplification and detection of DNA based on energy transfer. Nucleic Acids Res. 1997 Jun. 15;25(12):2516–21.

Ririe KM, Rasmussen RP, Wittwer CT. Product differentiation by analysis of DNA melting curves during the polymerase chain reaction. Anal Biochem. 1997 Feb. 15;245(2):154–60.

Tyagi S. Kramer FR. Molecular beacons: probes that fluoresce upon hybridization. Nat Biotechnol. 1996 Mar.; 14(3):303–8.

Wallace RB, Shaffer J, Murphy RF, Bonner J, Hirose T, Itakura K. Hybridization of synthetic oligodeoxyribonucleotides to phi chi 174 DNA: the effect to single base pair mismatch. Nucleic Acids Res. 1979 Aug. 10;6(11):3543–57.

Wetmur JG. DNA probes: application of the principles of nucleic acid hybridization. Crit Rev Biochem Mol Biol. 1991;26(3–4):227–59. Review.

Wittmer CT, Herrmann MG, Moss AA, Rasmussen RP. Continuous fluorescence monitoring of rapid cycle DNA amplification, Biotechniques. 1997 Jan.;22(1):130–1, 134–8.

Wu P, Brand L. Resonance energy transfer: methods and applications. Anal Biochem. 1994 Apr.;218(1):1–13. Review.

Figure 1. Melting Curves for Genotyping the Most Stable Mismatch

Figure 2. Continous (within cycle) monitoring of PCR with Hybridization and Exonuclease Probes Figure 3. Multiplexing by Color and Tm Figure 5. The Light Cycler™

Figure 6. Spectral Overlap between fluorescein, LC Red 640, CY5, Cy5.5

Figure 7. Emission Spectra of Resonance Energy Transfer Acceptors

Figure 8. Four Color Light Cycler™ - Optical Design

Figure 17.
Codon 6 Probe (LC Red 640)
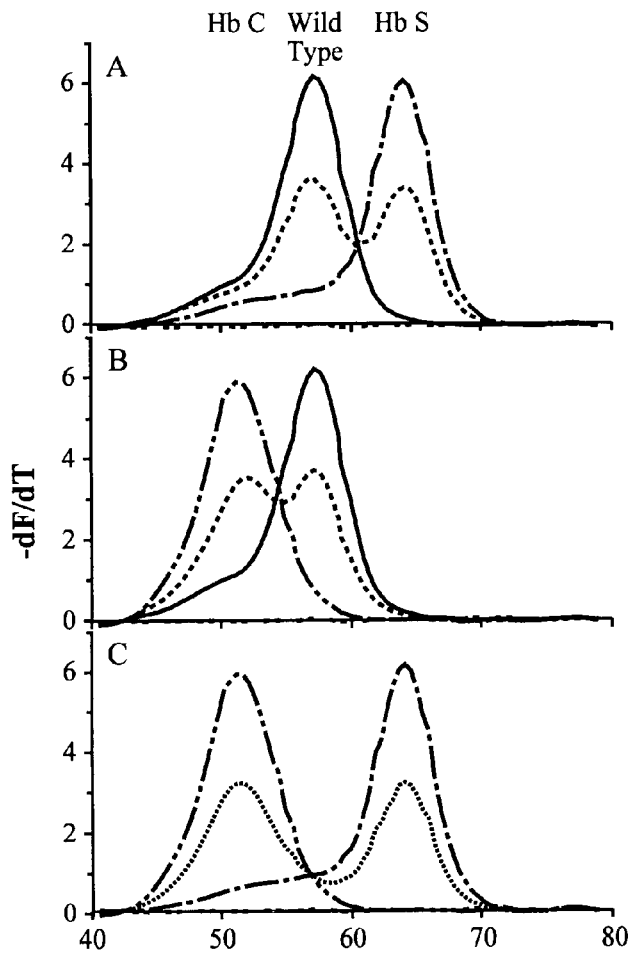
Codon 26 Probe (LC Red 705)
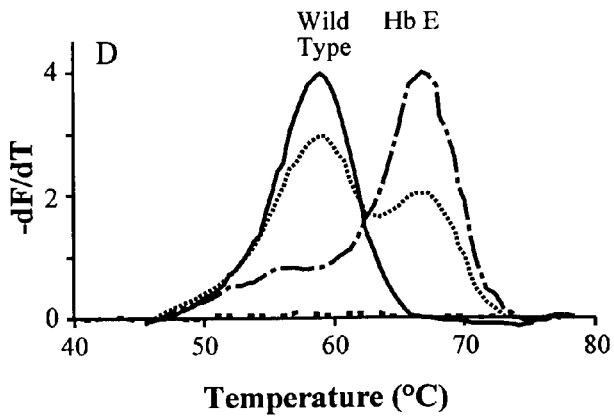

Sequence Variation and Probe Design at HLA-A

Figure 19. Predicted Tms for 2 Probes at a HLA-A Variable Reigon
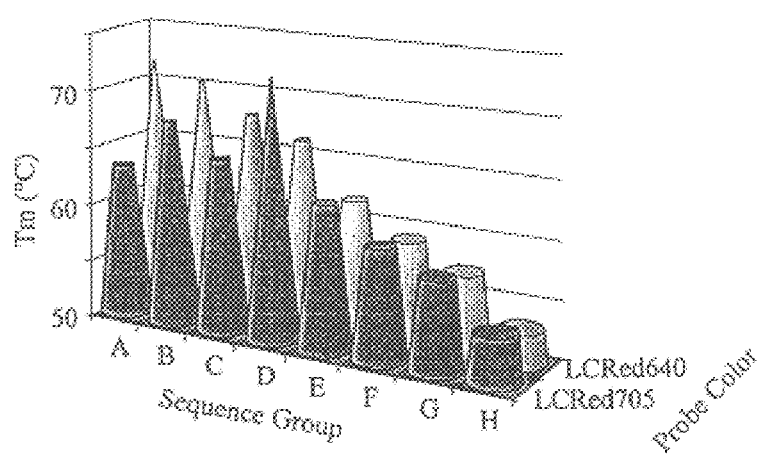

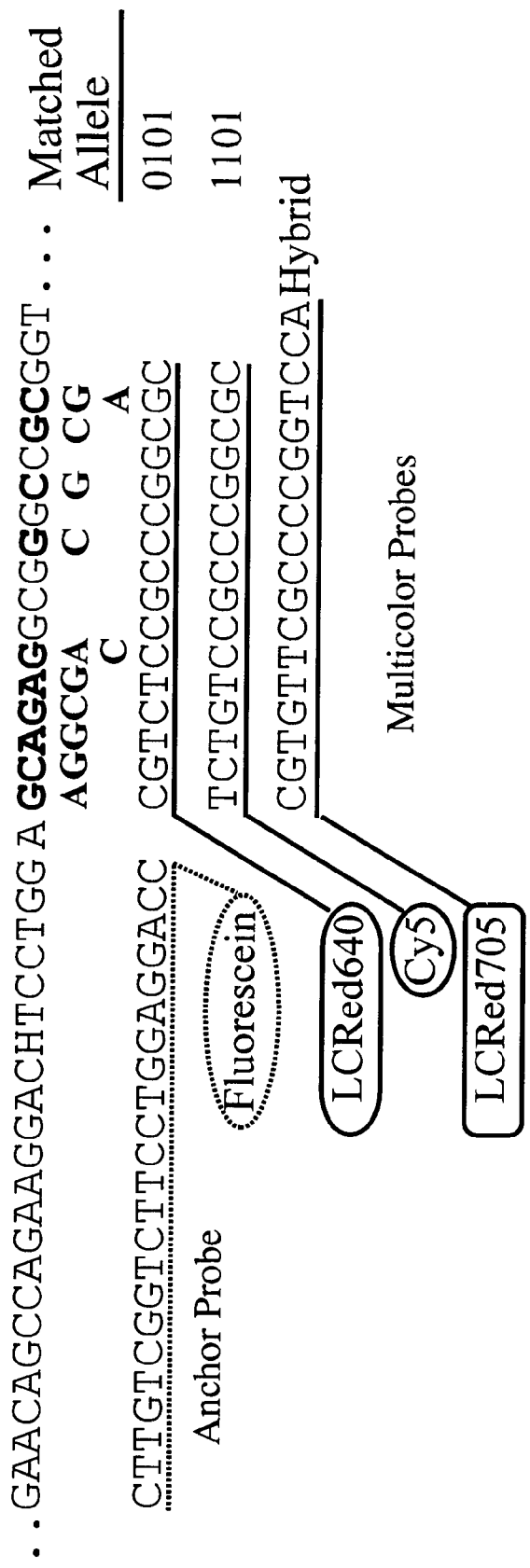
Figure 20. Sequence Variation and Probe Design at DRB1

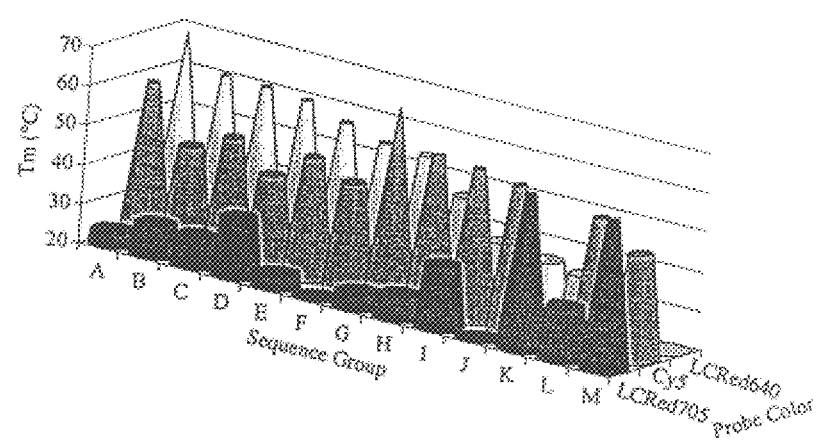
Figure 21. Predicted Tms for 3 Probes at a HLA DRB1 Variable Region

Figure 22. Scanning for Mutations ial patent application, Ser. No. 60/151,494, filed Aug. 30, 1999.

SEQUENCE LISTING

<160> NUMBER OF SEQ ID NOS: 30

<210> SEQ ID NO 1
<211> LENGTH: 56
<212> TYPE: DNA
<213> ORGANISM: Homo sapiens

<400> SEQUENCE: 1
ggcgcaggcc cggctgggcg cggacatgga ggacgtgtgc ggccgcctgg tgcagt       56

<210> SEQ ID NO 2
<211> LENGTH: 56
<212> TYPE: DNA
<213> ORGANISM: Homo sapiens

<400> SEQUENCE: 2
ggcgcaggcc cggctgggcg cggacatgga ggacgtgcgc ggccgcctgg tgcagt       56

<210> SEQ ID NO 3
<211> LENGTH: 17
<212> TYPE: DNA
<213> ORGANISM: Artificial Sequence
<220> FEATURE:
<223> OTHER INFORMATION: synthetic.

<400> SEQUENCE: 3
ccaggcggcc gcacacg                                                  17

<210> SEQ ID NO 4
<211> LENGTH: 30
<212> TYPE: DNA
<213> ORGANISM: Artificial Sequence
<220> FEATURE:
<223> OTHER INFORMATION: synthetic.

<400> SEQUENCE: 4
cctccatgtc cgcgcccagc cgggcctgcg                                    30

<210> SEQ ID NO 5
<211> LENGTH: 52
<212> TYPE: DNA
<213> ORGANISM: Homo sapiens

<400> SEQUENCE: 5
gcggctcctg cccgatgccg atgacctgca gaagtgcctg gccagtgtac ca           52

<210> SEQ ID NO 6
<211> LENGTH: 51
<212> TYPE: DNA
<213> ORGANISM: Homo sapiens

<400> SEQUENCE: 6
gcggctcctg cccgatgccg atgacctgca gaagcgcctg gcagtgtacc a            51

<210> SEQ ID NO 7
<211> LENGTH: 17
<212> TYPE: DNA
<213> ORGANISM: Artificial Sequence
<220> FEATURE:
<223> OTHER INFORMATION: synthetic.

<400> SEQUENCE: 7
acactgccag gcacttc                                                  17

<210> SEQ ID NO 8
<211> LENGTH: 27
<212> TYPE: DNA
<213> ORGANISM: Artificial Sequence
<220> FEATURE:
<223> OTHER INFORMATION: synthetic.

<400> SEQUENCE: 8
gcaggtcatc ggcatcgggc aggagcc                                27

<210> SEQ ID NO 9
<211> LENGTH: 19
<212> TYPE: DNA
<213> ORGANISM: Artificial Sequence
<220> FEATURE:
<223> OTHER INFORMATION: synthetic.

<400> SEQUENCE: 9
gtcagggcag agccatcta                                         19

<210> SEQ ID NO 10
<211> LENGTH: 24
<212> TYPE: DNA
<213> ORGANISM: Artificial Sequence
<220> FEATURE:
<223> OTHER INFORMATION: synthetic.

<400> SEQUENCE: 10
gttctattgg tctccttaaa ggtg                                   24

<210> SEQ ID NO 11
<211> LENGTH: 19
<212> TYPE: DNA
<213> ORGANISM: Artificial Sequence
<220> FEATURE:
<223> OTHER INFORMATION: synthetic.

<400> SEQUENCE: 11
ctcctgtgga gaagtctgc                                         19

<210> SEQ ID NO 12
<211> LENGTH: 19
<212> TYPE: DNA
<213> ORGANISM: Artificial Sequence
<220> FEATURE:
<223> OTHER INFORMATION: synthetic.

<400> SEQUENCE: 12
gttggtggta aggccctgg                                         19

<210> SEQ ID NO 13
<211> LENGTH: 35
<212> TYPE: DNA
<213> ORGANISM: Artificial Sequence
<220> FEATURE:
<223> OTHER INFORMATION: synthetic.

<400> SEQUENCE: 13
gttactgccc tgtggggcaa ggtgaacgtg gatga                       35

<210> SEQ ID NO 14
<211> LENGTH: 18
<212> TYPE: DNA
<213> ORGANISM: Artificial Sequence
<220> FEATURE:

<223> OTHER INFORMATION: synthetic.

<400> SEQUENCE: 14
gacagcgacg ccgcgagc                                                    18

<210> SEQ ID NO 15
<211> LENGTH: 19
<212> TYPE: DNA
<213> ORGANISM: Artificial Sequence
<220> FEATURE:
<223> OTHER INFORMATION: synthetic.

<400> SEQUENCE: 15
gggccggggt cactcaccg                                                   19

<210> SEQ ID NO 16
<211> LENGTH: 18
<212> TYPE: DNA
<213> ORGANISM: Artificial Sequence
<220> FEATURE:
<223> OTHER INFORMATION: synthetic.

<400> SEQUENCE: 16
agcgggtgcg gttcctgg                                                    18

<210> SEQ ID NO 17
<211> LENGTH: 26
<212> TYPE: DNA
<213> ORGANISM: Artificial Sequence
<220> FEATURE:
<223> OTHER INFORMATION: synthetic.

<400> SEQUENCE: 17
caaccccgta gttgtgtctg cagtag                                           26

<210> SEQ ID NO 18
<211> LENGTH: 214
<212> TYPE: DNA
<213> ORGANISM: Homo sapiens

<400> SEQUENCE: 18
agtcagggca gagccatcta ttgcttacat ttgcttctga cacaactgtg ttcactagca      60
acctcaaaca gacaccatgg tgcacctgac tcctgtggag aagtctgccg ttactgccct     120
gtggggcaag gtgaacgtgg atgaagttgg tggtgaggcc ctgggcaggt tggtatcaag     180
gttacaagac aggtttaagg agaccaatag aaac                                 214

<210> SEQ ID NO 19
<211> LENGTH: 214
<212> TYPE: DNA
<213> ORGANISM: homo

<400> SEQUENCE: 19
agtcagggca gagccatcta ttgcttacat ttgcttctga cacaactgtg ttcactagca      60
acctcaaaca gacaccatgg tgcacctgac tcctgaggag aagtctgccg ttactgccct     120
gtggggcaag gtgaacgtgg atgaagttgg tggtaaggcc ctgggcaggt tggtatcaag     180
gttacaagac aggtttaagg agaccaatag aaac                                 214

<210> SEQ ID NO 20
<211> LENGTH: 214
<212> TYPE: DNA
<213> ORGANISM: Homo sapiens

```
<400> SEQUENCE: 20
agtcagggca gagccatcta ttgcttacat ttgcttctga cacaactgtg ttcactagca      60
acctcaaaca gacaccatgg tgcacctgac tcctgaggag aagtctgccg ttactgccct     120
gtggggcaag gtgaacgtgg atgaagttgg tggtgaggcc ctgggcaggt tggtatcaag     180
gttacaagac aggtttaagg agaccaatag aaac                                 214

<210> SEQ ID NO 21
<211> LENGTH: 214
<212> TYPE: DNA
<213> ORGANISM: Homo sapiens

<400> SEQUENCE: 21
agtcaggcca gagccatcta ttgcttacat ttgcttctga cacaactgtg ttcactagca      60
acctcaaaca gacaccatgg tgcacctgac tcctaaggag aagtctgccg ttactgccct     120
gtggggcaag gtgaacgtgg atgaagttgg tggtgaggcc ctgggcaggt tggtatcaag     180
gttacaagac aggtttaagg agaccaatag aaac                                 214

<210> SEQ ID NO 22
<211> LENGTH: 184
<212> TYPE: DNA
<213> ORGANISM: Homo sapiens

<400> SEQUENCE: 22
gacagcgacg ccgcgagcca gaggatggag ccgcgggcrc cgtggatagr gcaggagrrk      60
cckgagtatt gggacsdgra sacasggmaw rtgaaggccc astcastcac agactgaccg     120
agagaacctg cggatcgcgc tccgctacta caaccagagc gaggccggtg agtgaccccg     180
gccc                                                                  184

<210> SEQ ID NO 23
<211> LENGTH: 42
<212> TYPE: DNA
<213> ORGANISM: Artificial Sequence
<220> FEATURE:
<223> OTHER INFORMATION: synthetic.

<400> SEQUENCE: 23
ccaatactcc ggcccctcct gctctatcca cggcgcccgc gg                         42

<210> SEQ ID NO 24
<211> LENGTH: 31
<212> TYPE: DNA
<213> ORGANISM: Artificial Sequence
<220> FEATURE:
<223> OTHER INFORMATION: synthetic.

<400> SEQUENCE: 24
gagtgggcct tcatattccg tgtctcctgg t                                     31

<210> SEQ ID NO 25
<211> LENGTH: 31
<212> TYPE: DNA
<213> ORGANISM: Artificial Sequence
<220> FEATURE:
<223> OTHER INFORMATION: synthetic.

<400> SEQUENCE: 25
gcgtgggcct tcacattccg tgtctccccg t                                     31
```

```
<210> SEQ ID NO 26
<211> LENGTH: 192
<212> TYPE: DNA
<213> ORGANISM: Homo sapiens

<400> SEQUENCE: 26
agcgggtgcg gttcctggac agatatttct ataaccaaga ggagtacgtg cgcttcgaca      60
gcgacgtggg ggagtaccgg gcggtgacgg agctggggcg gcctagcgcc gagtactgga     120
acagccagaa ggachtcctg garsrsrggc gsgscsvggt ggacacctac tgcagacaca     180
actacggggt tg                                                         192

<210> SEQ ID NO 27
<211> LENGTH: 23
<212> TYPE: DNA
<213> ORGANISM: Artificial Sequence
<220> FEATURE:
<223> OTHER INFORMATION: synthetic.

<400> SEQUENCE: 27
ccaggaggtc cttctggctg ttc                                              23

<210> SEQ ID NO 28
<211> LENGTH: 16
<212> TYPE: DNA
<213> ORGANISM: Artificial Sequence
<220> FEATURE:
<223> OTHER INFORMATION: synthetic.

<400> SEQUENCE: 28
cgcggcccgc ctctgc                                                      16

<210> SEQ ID NO 29
<211> LENGTH: 16
<212> TYPE: DNA
<213> ORGANISM: Artificial Sequence
<220> FEATURE:
<223> OTHER INFORMATION: synthetic.

<400> SEQUENCE: 29
cgcggcccgc ctgtct                                                      16

<210> SEQ ID NO 30
<211> LENGTH: 18
<212> TYPE: DNA
<213> ORGANISM: Artificial Sequence
<220> FEATURE:
<223> OTHER INFORMATION: synthetic.

<400> SEQUENCE: 30
acctggcccc gcttgtgc                                                    18
```

HOMOGENEOUS MULTIPLEX HYBRIDIZATION ANALYSIS BY COLOR AND TM

Priority is claimed to applicants' provisional patent application, Ser. No. 60/151,494, filed Aug. 30, 1999.

This invention was made with United States Government support under Grant No. GM-58983, awarded by the National Institute of Health. The United States Government has certain rights in the invention.

FIELD OF THE INVENTION

The present invention relates to methods and devices for analyzing nucleic acid samples for sequence variations at multiple loci. More particularly, the invention relates to the use of differential fluorescent emission and differential hybridization melting temperature of fluorescently labeled nucleotide probes to identify nucleic acid samples, including PC and LCR products, which have multiple potential sequences at multiple loci. The invention also relates to devices which allow simultaneous analysis of three or more fluorescent labels having different emission spectra.

BACKGROUND OF THE INVENTION

The continued discovery of novel genes provides a resource of genetic material for studying the association between genotype and disease. As databases for polymorphic markers and disease causing mutations continue to grow, there is an increasing need for procedures that can screen nucleic acid sequences for the presence of known polymorphisms and mutations. Optimally, the procedure should be capable of analyzing multiple DNA sites simultaneously (including nucleic acid loci that are physically separated by great distances) for the presence of mutations or polymorphisms.

Current methods for determining the genetic constitution of individuals (genotyping) include oligonucleotide ligation, allele-specific oligonucleotide hybridization, and PCR-restriction fragment length analysis. All these methods require time consuming multiple manual steps. One alternative method of genotyping uses the melting temperature of fluorescent hybridization probes that hybridize to a PCR-amplified targeted region of genome/nucleic acid sequence to identify mutations and polymorphisms.

The polymerase chain reaction (PCR) is a technique of synthesizing large quantities of a preselected DNA segment. The technique is fundamental to molecular biology and is the first practical molecular technique for the clinical laboratory. PCR is achieved by separating the DNA into its two complementary strands, binding a primer to each single strand at the end of the given DNA segment where synthesis will start, and adding a DNA polymerase to synthesize the complementary strand on each single strand having a primer bound thereto. The process is repeated until a sufficient number of copies of the selected DNA segment have been synthesized. During a typical PCR reaction, double stranded DNA is separated into its single strands by raising the temperature of the DNA containing sample to a denaturing temperature where the two DNA strands separate (i.e., the "melting temperature of the DNA") and then the sample is cooled to a lower temperature that allows the specific primers to attach (anneal), and replication to occur (extend). Currently preferred methods utilize a thermostable polymerase in the polymerase chain reaction. A preferred thermostable DNA polymerase for use in the PCR reaction is the Taq DNA Polymerase and derivatives thereof, including the Stoffel fragment of Taq DNA polymerase and KlenTaql polymerase (a 5'-exonuclease 1 deficient variant of Taq polymerase (see U.S. Pat. No. 5,436,149).

Other nucleic acid amplification procedures are also widely practiced. For example, the self-sustained sequence replication (3SR) reaction utilizes three enzymes. The 3SR method is described in Guatelli et al., PNAS (USA) 87:1874–1878 (1990) and Mueller et al., Histochem. Cell Biol. 108(4–5):431–437 (1997). A similar method is described in U.S. Pat. No. 5,399,491. Strand displacement amplification (SDA) is another method of isothermal nucleic acid amplification. SDA relies on primer-directed nicking activity of a restriction enzyme and strand replacement activity of a polymerase which is exonuclease-deficient. SDA is described in Walker et al., PNAS (USA) 89:392–396 (1992); Walker et al., Nucleic Acids Res. 20(7):1691–1696 (1992); Nadeau et al., Anal. Biochem. 276(2):177–187 (1999) and in U.S. Pat. Nos. 5,270,184, 5,422,252, 5,455, 166, and 5,470,723. Yet another method, rolling-circle amplification (RCA) utilizes DNA polymerase to replicate circularized oligonucleotides. RCA is described in Lizardi et al., Nat. Genet. 19(3):225–232 (1998) and U.S. Pat. No. 5,854,033. Each of the above-cited references is incorporated herein in its entirety.

Thermal cycling may be carried out using standard techniques known to those skilled in the art, including the use of rapid cycling PCR. Rapid cycling techniques are made possible by the use of high surface area-to-volume sample containers having relatively high thermal conductivity. The use of high surface area-to-volume sample containers allows for a rapid temperature response and temperature homogeneity throughout the biological sample. Improved temperature homogeneity also increases the precision of any analytical technique used to monitor PCR during amplification.

In a method compatible with the present invention, amplification of a nucleic acid sequence is conducted by thermal cycling the nucleic acid sequence in the presence of a thermostable DNA polymerase. The method comprises the steps of placing a biological sample comprising the nucleic acid sequence in a PCR vessel, raising the temperature of the biological sample from a first temperature to a second temperature, wherein the second temperature is at least 15° C. higher than the first temperature, holding the biological sample at the second temperature for a predetermined amount of time, lowering the temperature of the biological sample from the second temperature to at least the first temperature and holding the biological sample at a temperature at least as low as the first temperature for a predetermined length of time. The temperature of the biological sample is then raised back to the second temperature, and thermal cycling of the biological sample is repeated a predetermined number of times. In one embodiment, the method of amplifying a DNA sequence comprises a two temperature cycle wherein the samples are cycled through a denaturation temperature and an annealing temperature for a predetermined number of repetitions. However the PCR reaction can also be conducted using a three temperature cycle wherein the samples are cycled through a denaturation temperature, an annealing temperature and an elongation temperature for a predetermined number of repetitions.

In the state of the art for PCR, each temperature cycle of the PCR reaction is completed in approximately 60 seconds or less. Rapid cycling times can be achieved using the device and techniques described in U.S. Pat. No. 5,455,175, the disclosure of which is expressly incorporated herein.

PCR amplification of one or more targeted regions of a DNA sample has been conducted in the presence of fluorescently labeled hybridization probes, wherein the probes are synthesized to hybridize to a specific locus present in a target amplified region of the DNA. Many different probes are available for monitoring PCR each cycle. Dyes like ethidium bromide or SYBR Green I, which preferentially bind to double-stranded DNA, can be used in any amplification and a re inexpensive. Although not sequence specific, product specificity can be increased by analysis of melting curves (Ririe et al., *Anal. Biochem.* 245:154–160 (1997)), or by acquiring fluorescence at a high temperature where nonspecific products have melted (Morrison et al., *BioTechniques* 24(6):954–958, 960, 962 (1998)). However, multiplexing by color is not possible.

Multiplexing by color is possible with dual-labeled oligonucleotides, including hairpin primers (Sunrise™ primers), hairpin probes (Molecular Beacons™), and exonuclease probes (TaqMan™ probes). Hairpin primers include one fluorophore and one quencher (Nazarenko et al., *Nucl. Acids Res.* 25:2516–2521 (1997)). Hairpin probes hybridize internal to the primers and are sequence specific (Tyagi et al., *Nature Biotechnology* 14:303–308 (1996)). Exonuclease probes are cleaved during polymerase extension by 5'-exonuclease activity (Livak et al., *PCR Meth. Appl.* 4:357–362 (1995)). All these dual-labeled probes require careful design and are expensive. Their synthesis is difficult, requiring manual addition of at least one label and high pressure liquid chromatography for purification.

An alternative sequence specific method has been developed wherein two oligonucleotide probes that hybridize to adjacent regions of a DNA sequence are used (Wittwer et al., *BioTechniques* 22:130–138 (1997)). Each oligonucleotide probe is labeled with a respective member of a fluorescent energy transfer pair. In this method, the presence of the target nucleic acid sequence in a biological sample is detected by measuring fluorescent energy transfer between the fluorophores on the two labeled oligonucleotides. Such an energy transfer event is indicative of the presence of the target nucleic acid sequence.

SUMMARY OF THE INVENTION

The present invention provides methods and devices for analyzing sequence variations in nucleic acid samples using multiple colors. In one aspect, a method for analyzing a nucleic acid comprising multiple loci, each having two, three or more possible allelic sequences. The method involves combining at least a first and second pair of oligonucleotide probes with the nucleic acid sample. The first pair of probes is capable of hybridizing in proximity to each other within a segment of the nucleic acid sample comprising the first locus and the second pair is capable of hybridizing in proximity to each other within a segment of the nucleic acid sample comprising the second locus. The first member of each probe pair comprises a FRET donor and the second member comprises a FRET acceptor, the FRET acceptor of the first probe pair member having a different emission spectrum from the FRET acceptor of the second probe pair. Upon hybridization, the proximity of the first and second member of each probe pair is sufficient to allow fluorescence resonance energy transfer between the FRET donor and the FRET acceptor. At least one of the members of the first probe pair has a sequence which results in the differential hybridization of that member with at least two different alleles which may be present at the first locus and at least one of the members of said second pair has a sequence which results in the differential hybridization of that member with at least three different alleles which may be present at the second locus. The method further involves measuring the emission of each of the FRET acceptors at a first temperature and repeating those emission measurements at a second and third temperature. The emission of the FRET acceptors at different temperatures provides an indication of the alleles present at the first and second loci. In a preferred embodiment, the method further involves a third pair of oligonucleotide probes which is combined with the nucleic acid sample, wherein the FRET acceptor of each of the first, second and third probe pairs has an emission spectrum which is different from the emission spectrum of the others. In a preferred embodiment, the nucleic acid sample is the product of one or more reactions selected from the group consisting of PCR, 3SR, SDA and RCA. In a preferred embodiment, at least one probe pair member has two FRET acceptors, two FRET donors or a FRET acceptor and a FRET donor, and is a member of two different probe pairs.

In another aspect, the invention provides a method for analyzing a nucleic acid sample comprising three or more loci each having at least two different allelic sequences. This method involves combining at least a first, a second and a third pair of oligonucleotide probes with the nucleic acid sample, each of the members of the pairs being capable of hybridizing in proximity to each other within a segment of the nucleic acid sample comprising at least one of the multiple loci. The first member of each pair comprises a FRET donor and the second member comprises a FRET acceptor, wherein the FRET acceptor in the first pair has an emission spectrum which is different from the emission spectrum of the FRET acceptor in the second and third oligonucleotide probe pairs. When the second and third probe pairs have the same FRET acceptor, each of the second and third probe pairs has a different Tm from each other for each different allele within the nucleic acid sample segment to which each member hybridizes. Upon hybridization, the proximity of the probe pair members is sufficient to allow fluorescence resonance energy transfer between the FRET donor and the FRET acceptor. At least one of the members of each pair has a sequence which results in the differential hybridization of that member with at least two different alleles which may be present at said loci. The method further involves measuring the emission of each of the FRET acceptors at a first temperature and repeating those emission measurements at a second and third temperature. The emission of the FRET acceptors at different temperatures provides an indication of the alleles present at the multiple loci. In a preferred embodiment, the FRET acceptor of each of the second members of each of a first, a second and a third probe pair has an emission spectrum which is different from the emission spectrum of the others. In a preferred embodiment, the nucleic acid sample is the product of one or more reactions selected from the group consisting of PCR, 3SR, SDA and RCA. In a preferred embodiment, at least one probe pair member has two FRET acceptors, two FRET donors or a FRET acceptor and a FRET donor, and is a member of two different probe pairs.

In addition, provided herein is a method for analyzing a nucleic acid sample. The method involves contacting a nucleic acid sample comprising multiple loci with at least a first and a second primer, each of which is specific for one of said loci, under conditions which allow formation of at least a first and a second linear amplification product which are specific for each of said loci. The first amplification product contains one of at least two or more different allelic sequences which may be present at each of the loci within the first amplification product and the second amplification product contains one of at least three or more different allelic sequences which may be present at each of the loci within the second amplification product. Each of the amplification products comprises at least one member of a pair of FRET acceptor or FRET donor. The method further involves contacting each of the loci specific amplification products with FRET labeled oligonucleotide probes. Each of the FRET probes hybridizes with the amplification product at a segment encompassing a specific locus, wherein each of the probes has a sequence complementary to one of the allelic sequences which may be present at the specific locus within the amplification products and the hybridization product of each FRET probe with the other allelic sequences which may be present at the specific locus in the amplification products contains one or more mismatches, insertions or deletions which results in differential Tm of the FRET probe from each of the possible allelic sequences within that locus in the amplification products. Each of the FRET probes contains a member of a FRET donor and acceptor pair which is other than the FRET donor or acceptor contained in the corresponding specific amplification product. One of the FRET acceptors has an emission spectrum which is different from the emission spectrum of the other FRET acceptor. The primer sequences and oligonucleotide probe sequences are chosen so that upon hybridization the FRET donor and acceptor for each pair is in close proximity so as to allow fluorescence resonance energy transfer between the FRET donor and said FRET acceptor. The method further involves measuring the emission of each of the FRET acceptors at a first temperature and repeating those emission measurements at a second and third temperature. The emission of the FRET acceptors at different temperatures provides an indication of the alleles present at the multiple loci. In a preferred embodiment, the nucleic acid sample has three or more loci and is contacted with at least three primers under conditions which allow formation of at least three linear amplification products, and each of the FRET acceptors of a first, a second and a third probe donor and acceptor pair has an emission spectrum which is different from the emission spectrum of the others.

Also provided herein is a method for analyzing a nucleic acid sample comprising. This method involves contacting a nucleic acid sample having at least three loci with at least three primers, each of which are specific for one of the loci, under conditions which allow formation of at least three linear amplification products which are specific for each of the loci. Each of the amplification products contains one of at least two different allelic sequences which may be present at each of the loci. Each of the amplification products comprises at least one member of a FRET acceptor and FRET donor pair. The method further involves contacting each of the loci specific amplification products with FRET labeled oligonucleotide probes. Each of the FRET probes hybridizes with the amplification product at a segment encompassing a specific locus, and the hybridization product of each FRET probe with the other allelic sequences which may be present within that locus in the amplification products contains one or more mismatches, insertions or deletions which result in differential Tm of the probe from each of the possible allelic sequences within that locus in the amplification products. Each of the FRET probes contains a member of a FRET donor and acceptor pair which is other than the FRET donor or acceptor contained in the corresponding specific amplification product. One of the FRET acceptors has an emission spectrum which is different from the emission spectrum of the other FRET acceptor. When the FRET donor and acceptor combination of different probes is the same, the Tm of the probe pairs from each different allele within the nucleic acid segment to which each probe hybridizes is different. The primer sequences and oligonucleotide probe sequences are chosen so that upon hybridization the FRET donor and acceptor for each pair is in close proximity so as to allow fluorescence resonance energy transfer between the FRET donor and the FRET acceptor. The method further involves measuring the emission of each of the FRET acceptors at a first temperature and repeating those emission measurements at a second and third temperature. The emission of the FRET acceptors at different temperatures provides an indication of the alleles present at the first and second loci. In a preferred embodiment, each FRET acceptor of the FRET donor and acceptor combination for a first, a second and a third probe has an emission spectrum which is different from the others.

In consideration of each of the methods described above, in a preferred embodiment, measurements of FRET acceptor emission is measured throughout a range of temperatures, preferably from at least 20° C. to at most 95° C., preferably at least every 0.1 to 10 seconds, preferably while varying the temperature at least 0.01 to 1° C. per second. In a preferred embodiment, emission measurements at a particular temperature are simultaneous. In a preferred embodiment, at least one of the FRET acceptors is selected from the group consisting of LC Red 640, Cy 5, Cy 5.5 and LC Red 705. In a preferred embodiment, emission measurements are corrected for spectral overlap between or among the different fluorophores.

In another aspect of the invention, a device is provided for multichannel color analysis of a PCR or LCR reaction. The device comprises a chamber for holding a nucleic acid amplification reaction product comprising an optically transparent wall. The device further comprises a source for providing electromagnetic radiation to said optically transparent wall. In addition, the device has at least four bandpass filters at least two of which are not coplanar. The filters are positioned to simultaneously or sequentially filter fluorescence emissions from the chamber so as to provide filtered multichannel fluorescence signals. Also, the device comprises an optical detector positioned to receive the filtered emission signals. In a preferred embodiment, the bandpass filters which are not coplanar are orthogonal to each other. In a preferred embodiment, the chamber comprises a nucleic acid amplification reaction chamber.

In yet another aspect, the invention provides a device for multichannel color analysis of a nucleic acid amplification reaction. The device comprises a chamber for holding a nucleic acid amplification reaction product comprising an optically transparent wall. The device also comprises a source for providing electromagnetic radiation to said optically transparent wall and at least three dichroic filters and two bandpass filters. The bandpass filters are not coplanar and the dichroic filters are positioned so that the emissions passing through each bandpass filter intersect each others path to simultaneously or sequentially filter florescence emissions from the reaction chamber, thus providing filtered multichannel florescence signals. In addition, the device comprises an optical detector positioned to receive the filtered emission signals. In a preferred embodiment, the chamber comprises a nucleic acid amplification reaction chamber.

Other aspects of the invention will become apparent to the skilled artisan from the following description of the invention.

The orthogonal configuration equalizes the number of optical elements that light in each channel must cross. The maximum number of elements and the pathlength of the longest wavelength dye are reduced, decreasing optical losses and alignment difficulty. The paths of Cy5 and fluorescein fluorescence cross in space. There is exact temporal coincidence.

The filter wheel design minimizes optical losses and costs. The number of lenses is reduced from 6 (linear and orthogonal) to 3. The number of dichroics and mirrors is reduced from 5 (linear) or 4(orthogonal) to 1. Only one detector needs to be aligned. All colors cannot be collected simultaneously. This introduces a temporal variation not present in the other designs. For multicolor acquisition, the filter wheel must be sequentially turned to each color for each sample.

Figure 9:
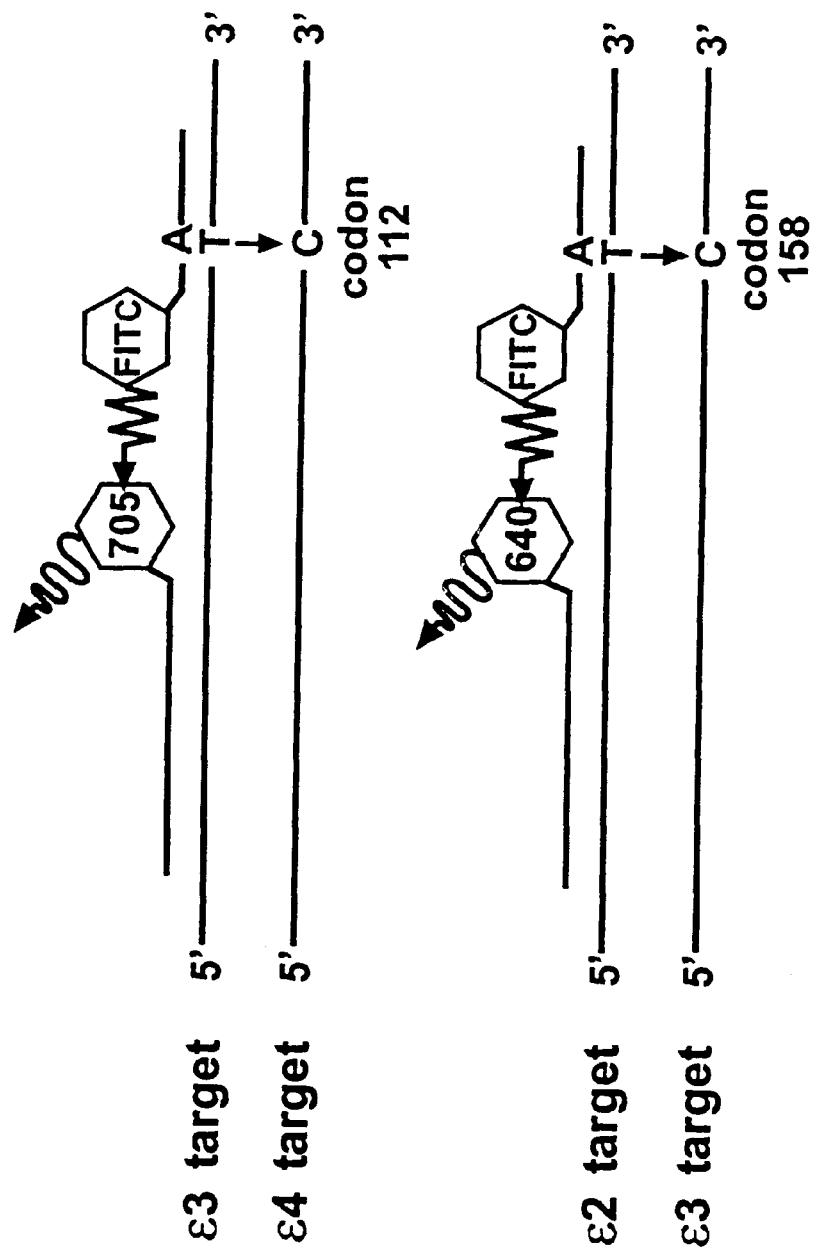

FIG. 9 shows a schematic representation of multicolor hybridization probe genotyping at the apolipoprotein E locus. Allele determining nucleotide bases are shown. Full sequences of the unlabeled oligonucleotide strands and fluorescently labeled probes are provided in Table I. Fluorescence resonance energy transfer is observed during adjacent hybridization of 3'-fluorescein labeled and 5'-acceptor labeled probes to target strands. The $\epsilon3/\epsilon4$ allele determining base within codon 112 is spanned by a fluorescein labeled probe that is coupled with a 5'-LC Red 705 labeled probe. Similarly, the nucleotide distinguishing the $\epsilon3$ from the $\epsilon2$ allele at codon 158 is spanned by a fluorescein labeled probe coupled with a 5'-LC Red 640 labeled probe. The fluorescein labeled probes form destabilizing A:C mismatches when hybridized to the $\epsilon4$ allele at codon 112 or the $\epsilon3$ allele at codon 158.

Figure 10:
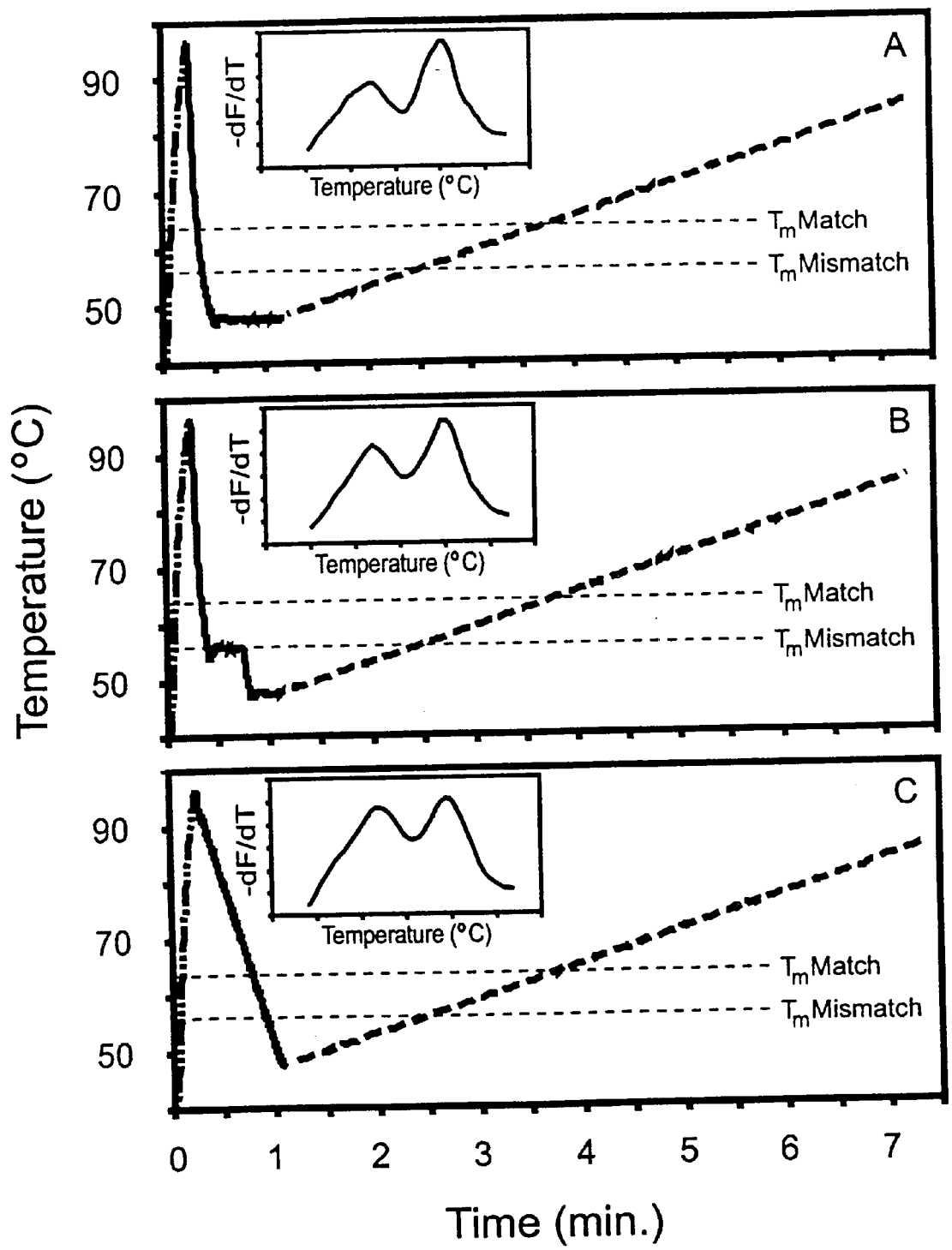

FIG. 10 shows Alternate temperature traces and resultant melting curve analysis at the Apo E locus. Three different genotyping protocols (A, B, and C) varied only in the temperature/time conditions for annealing (solid line). Protocol A used rapid cooling at 20° C./s down to a temperature 8° C. below the Tm of the mismatched duplex, followed by a 40 s hold at the target temperature (48° C. for codon 158, 54° C. for codon 112). Protocol B cooled with rapid temperature transitions (20° C./s) interrupted by 20 s holds at temperatures 8° C. below the Tm of both matched and mismatched duplexes (56° C. and 48° C. for codon 158, 62° C. and 54° C. for codon 112). Protocol C was performed using a slower temperature transition rate (1° C./s) to a temperature 8° C. below the Tm of the mismatched duplex (48° C. for codon 158, 54° C. for codon 112) and the melting phase began without a hold at the target temperature. Protocol C was also used for multiplex genotyping with the melting phase starting at 42° C. The denaturation phase alternating dots and dash) for all protocols consisted of rapid heating from room temperature up to 94° C. and melting curves (insets) were generated during heating (broken line) at 0.1° C./s from the target temperature up to 85° C. The general trend proceeding from Protocol A-C is an increase in the peak area for the melting of the mismatched duplex. Although inset data for codon 158 are shown, this effect was observed at both sites.

Figure 11:
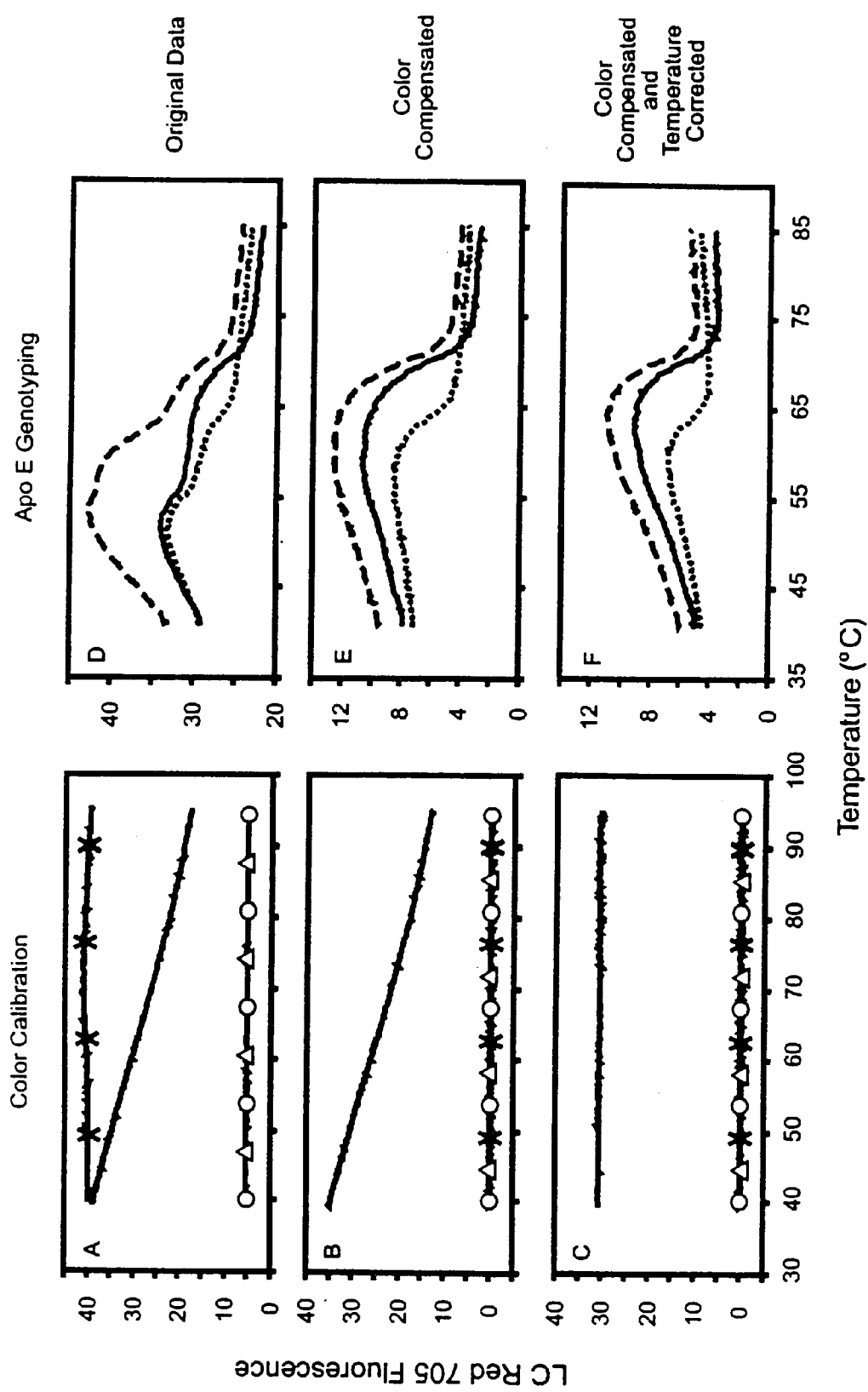

FIG. 11 shows calibration and application of color compensation for spectral overlap. Compensation of an extreme case of LC Red 640 spillover into the LC Red 705 channel is shown. Instrument gains were 1, 30, and 50 for fluorescein, LC Red 640, and LC Red 705 channels respectively. For the calibration run, the concentration of the labeled probes were 0.1 $\mu$M fluorescein (circle in line), 2 $\mu$M LC Red 640 (x in line), and 2 $\mu$M LC Red 705 (solid line) in 50 mM Tris, pH 8.5 (25° C.), 1 mM $MgCl_2$ and 250 $\mu$g/ml bovine serum albumin. A sample containing buffer without probes (triangle in line) was also included as a blank. Plot A shows the original color calibration data, plot B shows the calibration data after color compensation and plot C displays temperature correction to 50° C. after color compensation. The compensation and correction algorithms were then applied to the LC Red 705 channel in a multiplex color assay. Fluorescence vs. temperature curves are shown in plots D, E, and F and the same data displayed as –dF/dT vs. temperature in FIG. 14. The genotypes shown are: homozygous $\epsilon4$/homozygous $\epsilon3$ (dashed line), homozygous $\epsilon3$/homozygous $\epsilon3$ (broken line) and homozygous $\epsilon3$/heterozygous $\epsilon2/\epsilon3$ (solid line).

Figure 12:
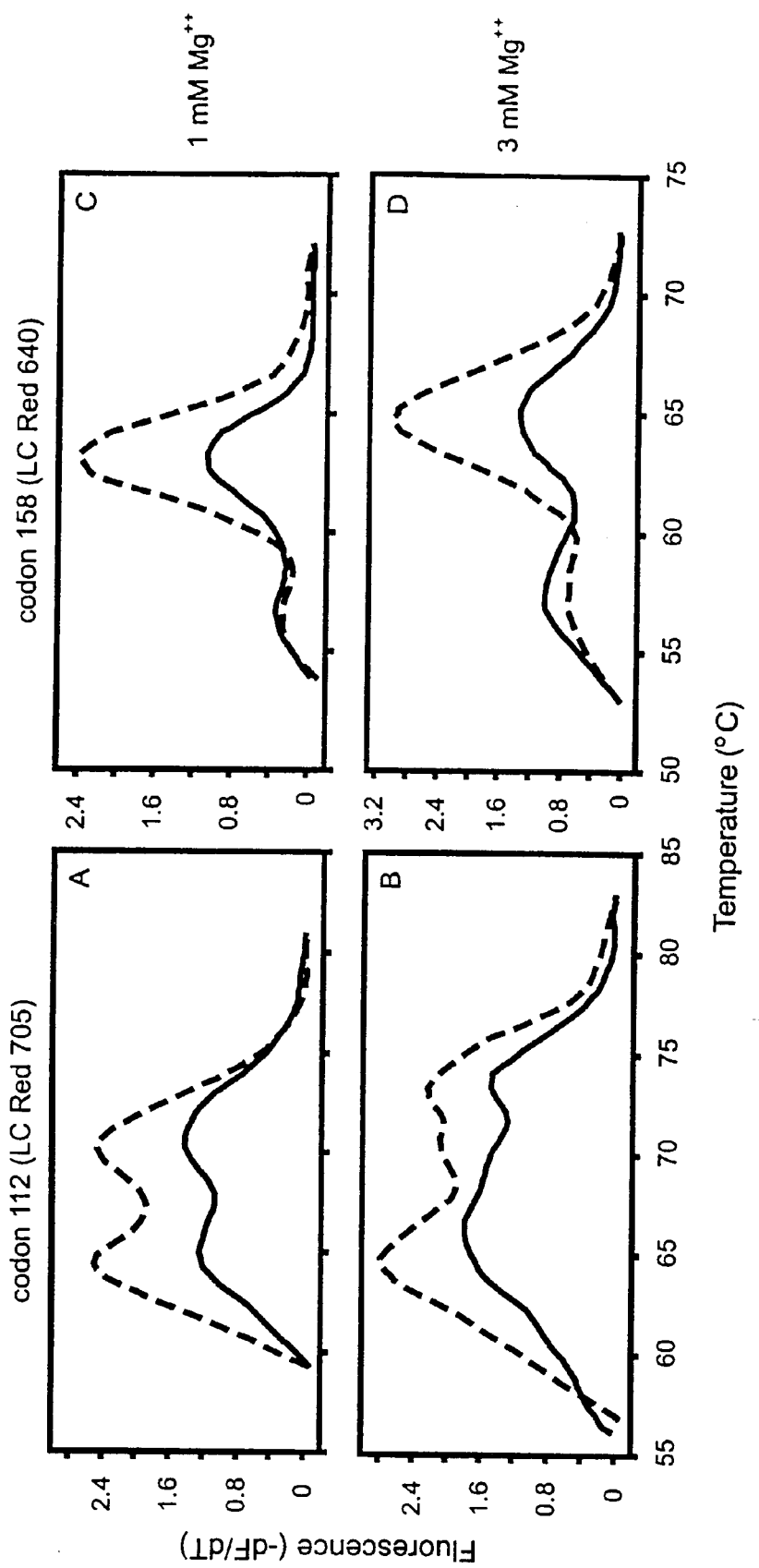

FIG. 12 shows optimization of target oligonucleotide and MgCl₂ concentrations for genotyping codons 112 and 158 of the Apo E gene. The temperature protocol of FIG. 12C was used for each site. The loss of fluorescence from the LC Red 705 (A and B) and LC Red 640 (C and D) acceptor probes during melting of an adjacent fluorescein labeled probe is plotted as –dF/dT vs. temperature as previously described (Bernard et al., *Am. J. Pathol.* 153, 1055–1061 (1998)). Each graph compares heterozygous melting peaks with targets present at either 0.05 µM (solid line) or 0.2 µM (broken line). Graphs A and C display genotyping using 1 mM Mg++ while 3 mM Mg++ was used in graphs B and D. The fluorescein probes were used at 0.1 µM and the acceptor probes at 0.2 µM. The competitor strands at each site were not present.

Figure 13:
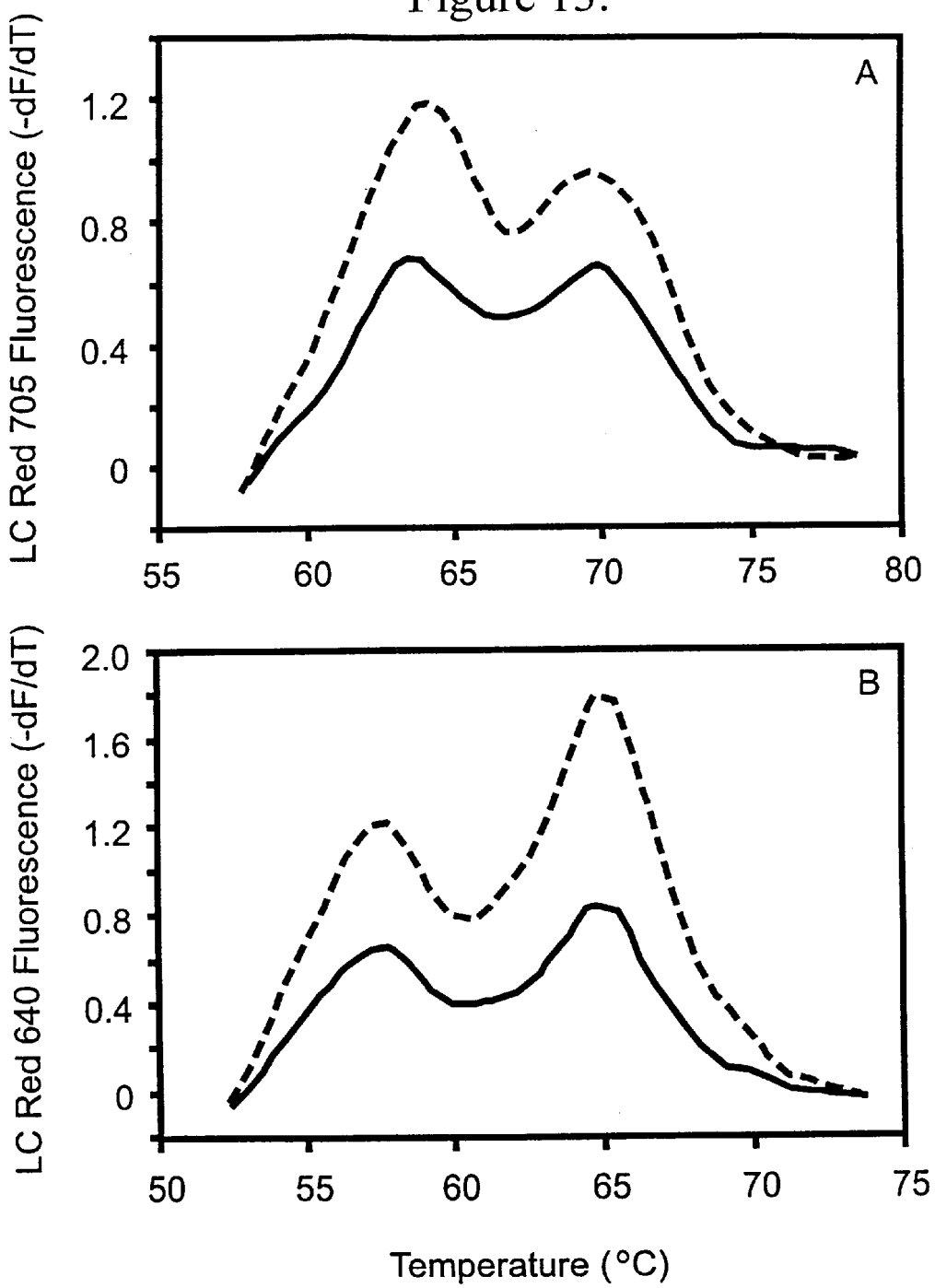

FIG. 13 illustrates competition during genotyping of Apo E targets in the presence of complementary strands. The temperature protocol of FIG. 10C was used for each site. The fluorescence derivative vs. temperature is plotted for each site as in FIG. 12 and as previously described (Bernard et al.(1998)). Heterozygous melting peaks at each site are shown. Graph A and B represent genotyping the ε3/ε4 alleles (codon 112) and the ε2/ε3 alleles (codon 158), respectively, in the presence (solid line) and absence (broken line) of competitor strands. For each site, the reagents include 0.1 µM fluorescein labeled probe, 0.2 µM reporter probe, 0.05 µM heterozygous targets with or without 0.05 µM competitor and either 1 mM Mg++ (codon 112) or 3 mM Mg++ (codon 158).

Figure 14:
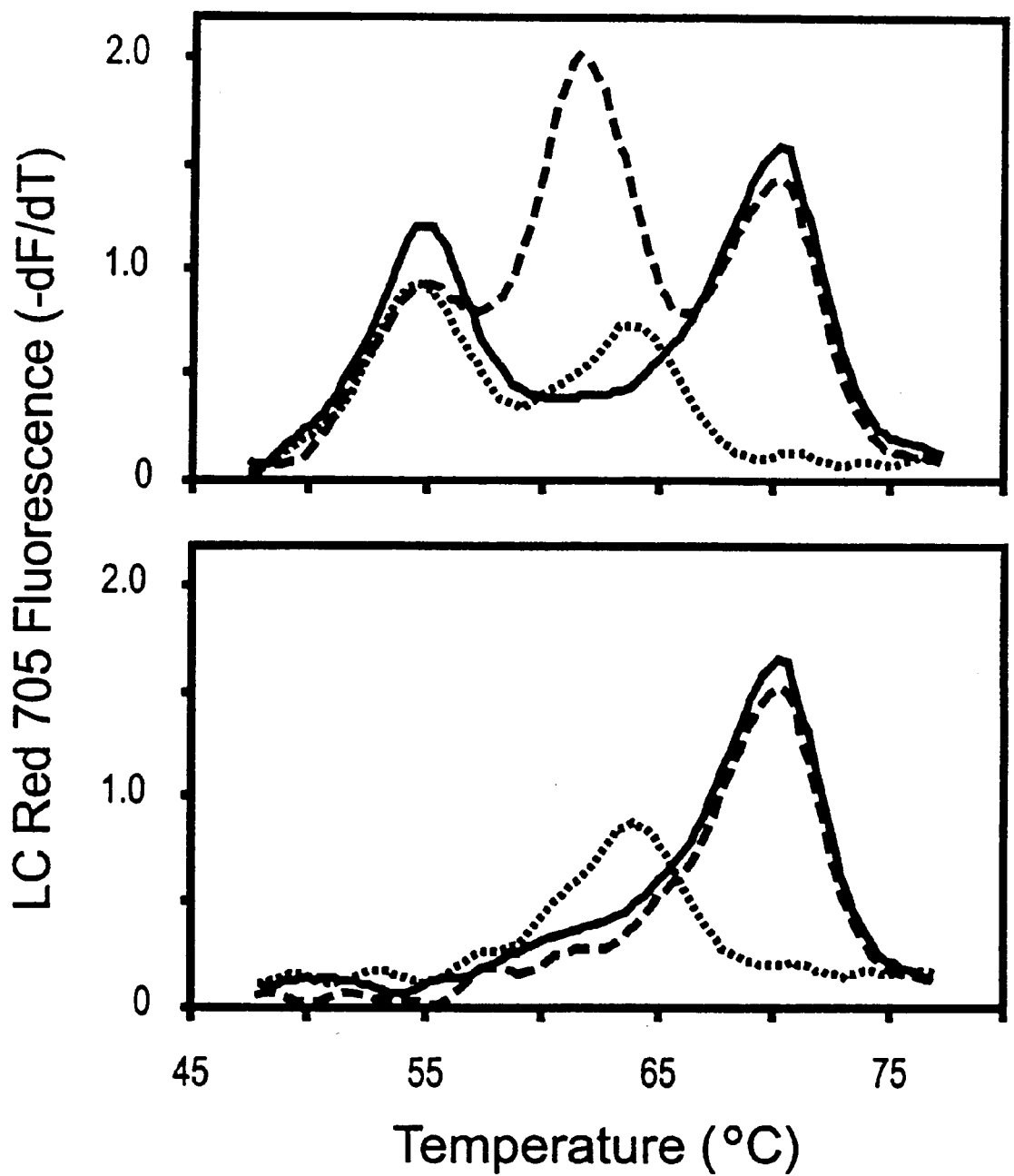

FIG. 14 shows multiplex color genotyping of codons 112 and 158 without competitor strand. The reagents used are described in Example 1. Temperature parameters are given in FIG. 10C. The uncompensated (A) and compensated (B) derivative melting curve data (plotted as dF/dT vs. temperature) is shown for the LC Red 705 channel used for analysis of codon 112. The uncompensated data displays melting peaks from codon 158 due to bleed over from the LC Red 640 acceptor dye. The compensated data shows only the genotypes at codon 112. The genotypes shown are: homozygous ε4/homozygous ε3 (dashed line), homozygous ε3/homozygous ε3 (broken line) and homozygous ε3/heterozygous ε2/ε3 (solid line).

Figure 15:
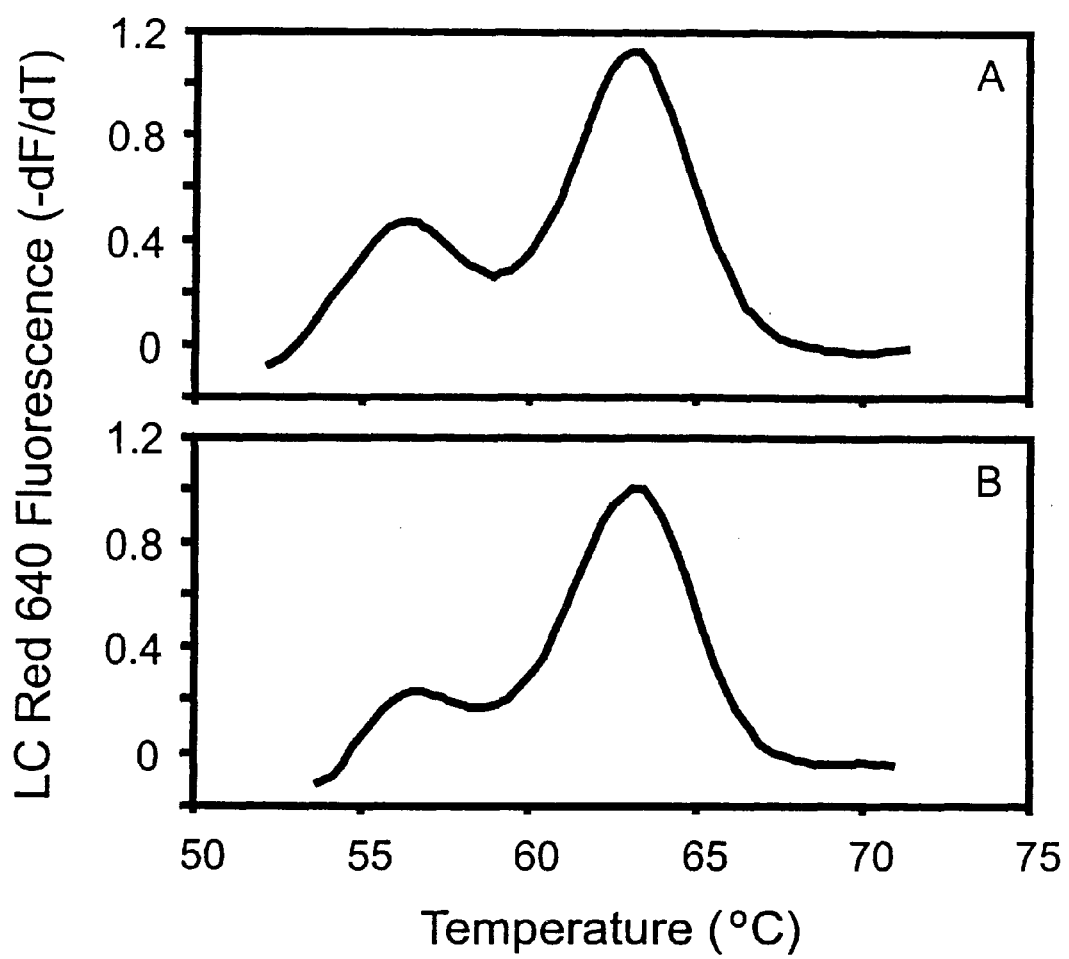

FIG. 15 shows the effect of a lower annealing temperature on peak area for the mismatched (ε3) target at codon 158. Graphs A and B represent genotyping of a heterozygous ε2/ε3 sample. The fluorescence derivative vs. temperature is plotted for the LC Red 640 probe as in FIG. 12. Graph A shows genotyping after cooling at 1° C./s to 42° C., the temperature used for multiplexing (FIG. 14). Graph B shows genotyping after cooling at 1° C./s to 48° C., the temperature used for genotyping optimization at codon 158.

Figure 16:
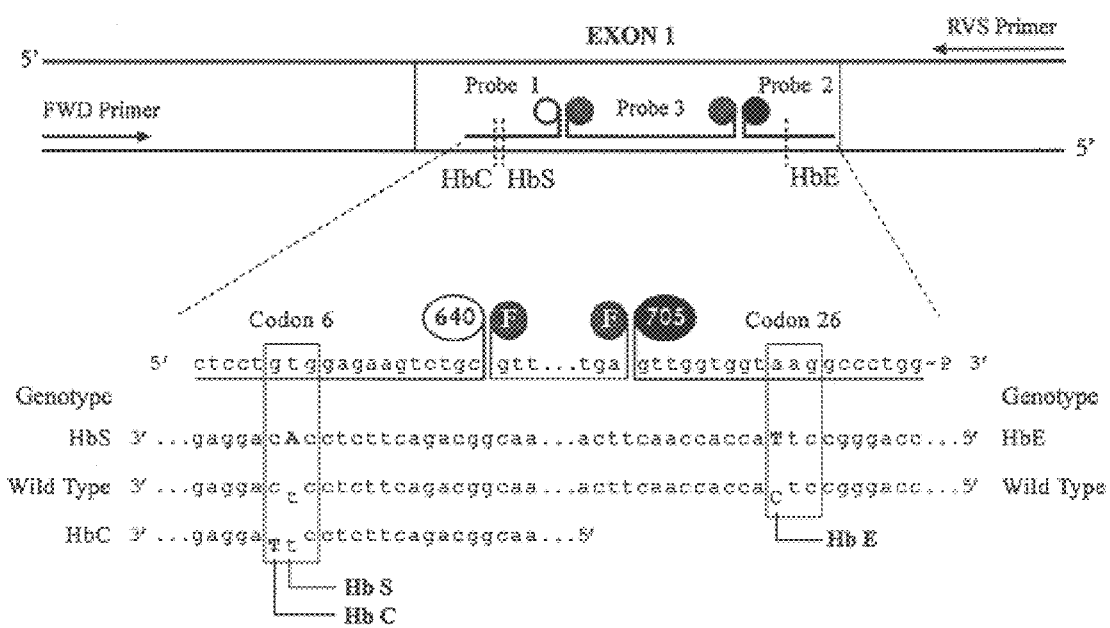

FIG. 16 (SEQ ID NOS. 11–13, and 18–21) shows a schematic for β-globin genotyping. A 214 bp fragment of the βglobin gene is illustrated. The sense and anti-sense DNA strands are shown with exon 1 centrally located. Arrows indicate forward and reverse primers. Mutation probes are indicated as Probe 1 (LC Red 640 labeled) for codon 6 and Probe 2 (LC Red 705 labeled) for codon 26. The dual-labeled fluorescein probe is positioned between Probes 1 and 2 Point mutations are indicated by bold capitalized script and duplex mismatches by subscripts.

FIG. 17 shows –dF/dT derivative melting curves for each β-globin detection drobe. Panels A–C contains –dF/dT derivative melting curves for genotypes detected by the codon 6 probe labeled with LC Red 640. Panel A shows wild type (solid line), homozygous Hb S (dash-dot-dash line), and S-trait (dotted line) –dF/dT melting curves. Panel B shows –dF/dT melting curves of wild type (solid line), homozygous Hb C (dash-dot-dot-dash line), and C-trait (dotted line). Panel C shows –dF/dT melting curves of compound heterozygote Hb S/C (dotted line) in comparison with homozygous Hb S (dash-dot-dash line), and Hb C (dash-dot-dot-dash line). Panel D contains –dF/dT derivative melting curves for genotypes detected by the codon 26 probe labeled with LC Red 705: wild type (solid line), homozygous Hb E (dash-dot-dash line), and E-trait (dotted line). A no template control (broken line) is present in all panels.

Figure 18:
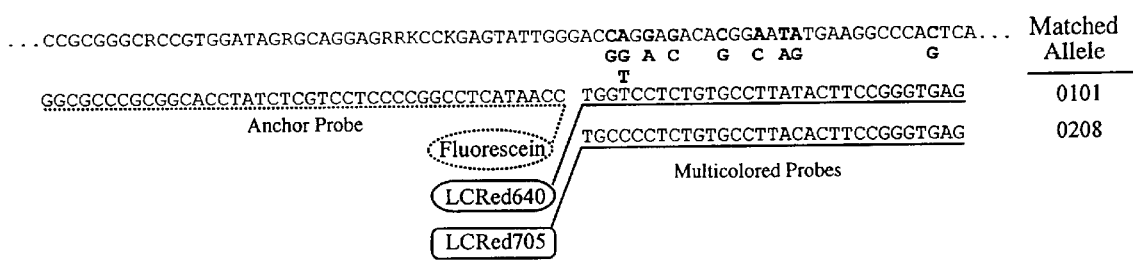

FIG. 18 (SEQ ID NOS:22–25) shows a schematic of probes to investigate one of the hyper-variable regions in HLA-A, at codons 62–67 in exon 2. Variable bases are indicated in bold type. Just upstream of this region is an area that is mostly conserved among the various HLA-A alleles. We will synthesize one fluoresce in donor probe and two acceptor probes, one labeled with LC Red640 and one with LC Red705.

FIG. 19 shows predicted Tm's for the two probes shown in FIG. 18 for each of 8 HLA-A alleles.

FIG. 20 (SEQ ID NOS:26–30) shows a schematic of probes for investigating variation within the HLA-DRB1 region by color and Tm multiplexing, Codons 70–74 of exon 2 are hyper-variable and adjacent to a conserved region.

FIG. 21 shows predicted Tm's for the three probes shown in FIG. 20 for each of 13 HLA-DRB1 alleles.

FIG. 22 shows 5 tandem hybridization probes with equal Tms (shown as equal lengths) to be used for scanning regions of nucleic acid for mutations. Using this embodiment, determining which FRET acceptor emissions are affected identifies the probe the mutation destabilizes. In some cases, the exact mutation may be identified by the Tm shift observed.

DETAILED DESCRIPTION OF THE INVENTION

The present invention is directed to the analysis of sequence variations in multiple loci of a nucleic acid sample. In one aspect, the invention provides methods of multiplex analysis of nucleic acid samples by color and Tm, using nucleic acid probes bearing different flourescent labels and having melting temperatures that are related to the sequences with which they hybridize. The use of both Tm and color allows for the investigation of a large number of sequences that may be found in a nucleic acid sample, including variants at a particular locus and sequences at several different loci. The number of sequences that can be analyzed is the product of the number of colors used and the number of Tm's distinguished. The only limit is the ability to differentiate the colors and the Tm's. The invention has many practical applications, including applications in the clinical laboratory. For example, multiple mutations may be analyzed simultaneously, which is particularly useful when one considers that most genetic disorders and cancers are caused by multiple mutations. Expected as well as unexpected polymorphisms can be detected. The invention may also be used to test for multiple infectious agents in a sample. The methods disclosed herein are particularly well suited for analyzing PCR and LCR products.

The ability to multiplex PCR analysis by color and Tm greatly extends the power of monitoring PCR with fluorescence. Many uses are apparent. For example, internal amplification controls are often needed for infectious disease and translocation testing to verify that amplifiable DNA or cDNA was present even if the target amplification is negative. Another common need is for multiplexing a competitor as an internal standard for quantification. Multiplexing also allows multiple amplicons, or multiple mutations within a single amplicon, to be analyzed independently in a single reaction mixture.

In another aspect, the invention provides devices which allow continuous and simultaneous analysis of several different fluorescent emission colors. The multichannel color analysis devices of the present invention, in combination with the methods, provide for multiplex analysis of multiple nucleic acid amplification products continuously throughout a reaction. The devices of the present invention provide a means for practicing the present methods under optimal conditions for determining Tm.

In general, the method of the invention involves combining fluorescently labeled oligonucleotide probes with a nucleic acid sample such that they hybridize, which hybridization allows fluorescence resonance energy transfer between the flurphore on the probe and a second fluorophore. The emission from the acceptor fluorophore is then measured at different increasing temperatures. The Tm is determined to be that temperature at which there is an abrupt reduction in emission. The color of the emission and the Tm are used to determine the sequence present in the nucleic acid sample.

Fluorescence resonance energy transfer (FRET) occurs between two fluorophores when they are in physical proximity to one another and the emission spectrum of one fluorophore overlaps the excitation spectrum of the other. The rate of resonance energy transfer is:

$(8.785 \mathrm{E}^{-5}) (t-1) (k^2) (n^{-4}) (q_D) (R^{-6}) (J_{DA})$, where:

t=excited state lifetime of the donor in the absence of the acceptor;

$k^2$=an orientation factor between the donor and acceptor;

n=refractive index of the visible light in the intervening medium;

$q_D$=quantum efficiency of the donor in the absence of the acceptor;

R=distance between the donor and acceptor measured in Angstroms;

$J_{DA}$=the integral of $(F_D)$ $(e_A)$ $(W^4)$ with respect to W at all overlapping wavelengths with:

$F_D$=peak normalized fluorescence spectrum of the donor;

A=molar absorption coefficient of the acceptor ($M^{-1}$ $cm^{-1}$);

$W^4$=wavelength (nm).

For any given donor and acceptor, a distance where 50% resonance energy transfer occurs can be calculated and is abbreviated $R_0$. Because the rate of resonance energy transfer depends on the 6th power of the distance between donor and acceptor, resonance energy transfer changes rapidly as R varies from $R_0$. At 2 $R_0$, very little resonance energy transfer occurs, and at 0.5 $R_0$, the efficiency of transfer is nearly complete, unless other forms of de-excitation predominate.

Using the method of Wittwer et al. (1997), fluorescently labeled oligonucleotides have been designed to hybridize to the same strand of a DNA sequence, resulting in the donor and acceptor fluorophores being separated by a distance ranging from about 0 to about 25 nucleotides, more preferably about 0–5 nucleotides, and most preferably about 0–2 nucleotides. A particularly preferred spacing between the donor and acceptor fluorophores is about 1 nucleotide.

When one of the labeled oligonucleotides also functions as a PCR primer ("probe-primer"), then the two fluorescently labeled oligonucleotides hybridize to opposite strands of a DNA sequence. In this embodiment, the donor an acceptor fluorophores are preferably within about 0–15 nucleotides and more preferably within about 4–6 nucleotides.

When both of the fluorescently labeled oligonucleotides are not hybridized to their complementary sequence on the targeted DNA, then the distance between the donor fluorophore and the acceptor fluorophore is too great for resonance energy transfer to occur. Thus the acceptor fluorophore and the donor fluorophore are not in resonance energy transfer relationship and excitation of the donor fluorophore will not produce a detectable increased fluorescence by the acceptor fluorophore.

Acceptable fluorophore pairs for use as fluorescent resonance energy transfer pairs are well know to those skilled in the art and include, but are not limited to, fluorescein/rhodamine, phycoerythrin/Cy7, fluorescein/Cy5 or fluorescein/Cy5.5.

Figure 1:
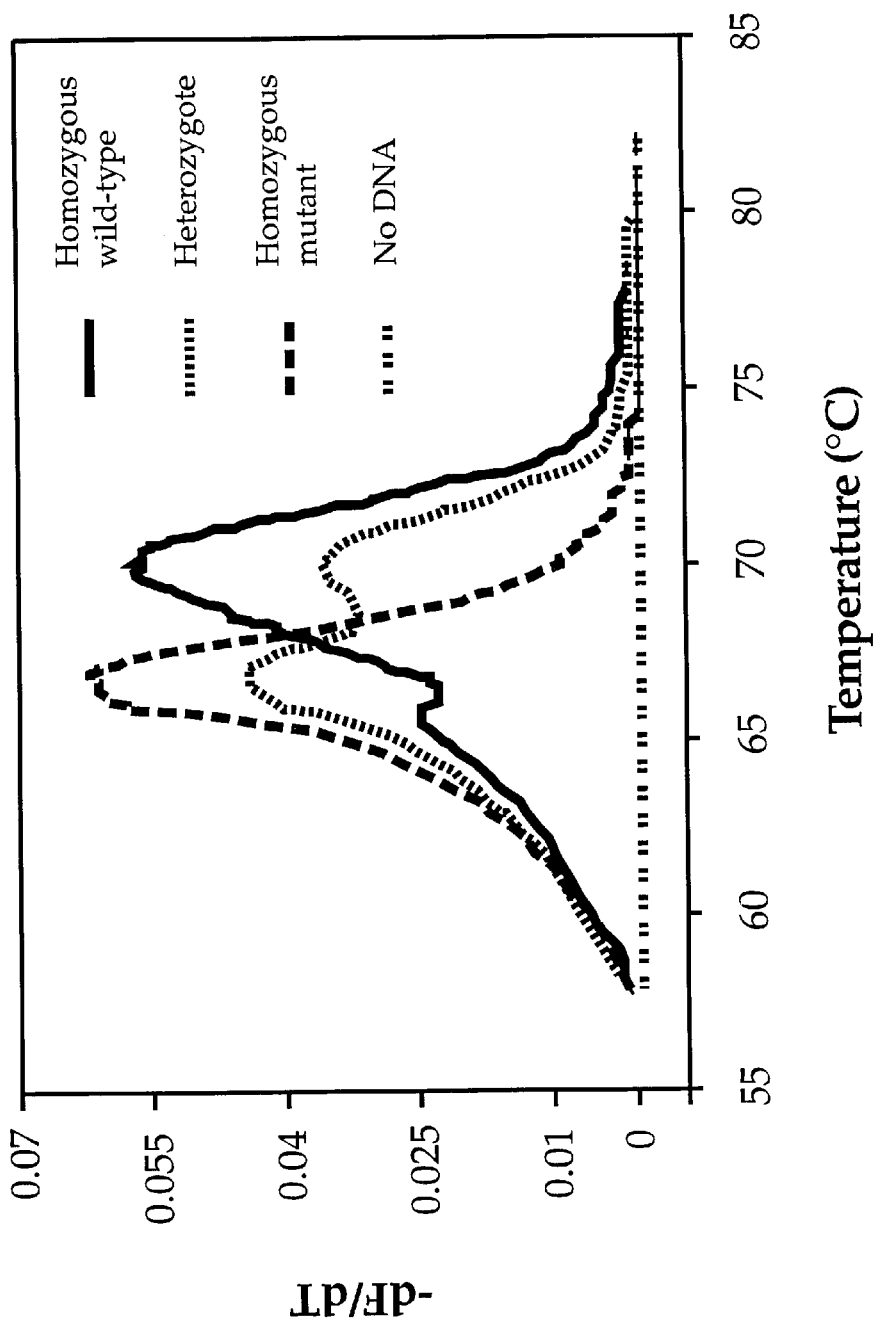
FIG. 1 shows melting curves for genotyping the homozygous wild type, heterozygote and homozygous mutant for the common thermolabile mutation in the methylenetetrahydrofolate reductase gene (Bernard et al., *Anal. Biochem.* 255:101–107 (1998)). This is an example of the most stable mismatch (a G-T mismatch flanked by G-C pairs). Perfect correlation with conventional genotyping techniques was observed. The Tm shift from the mismatch was 3° C.
Figure 2:
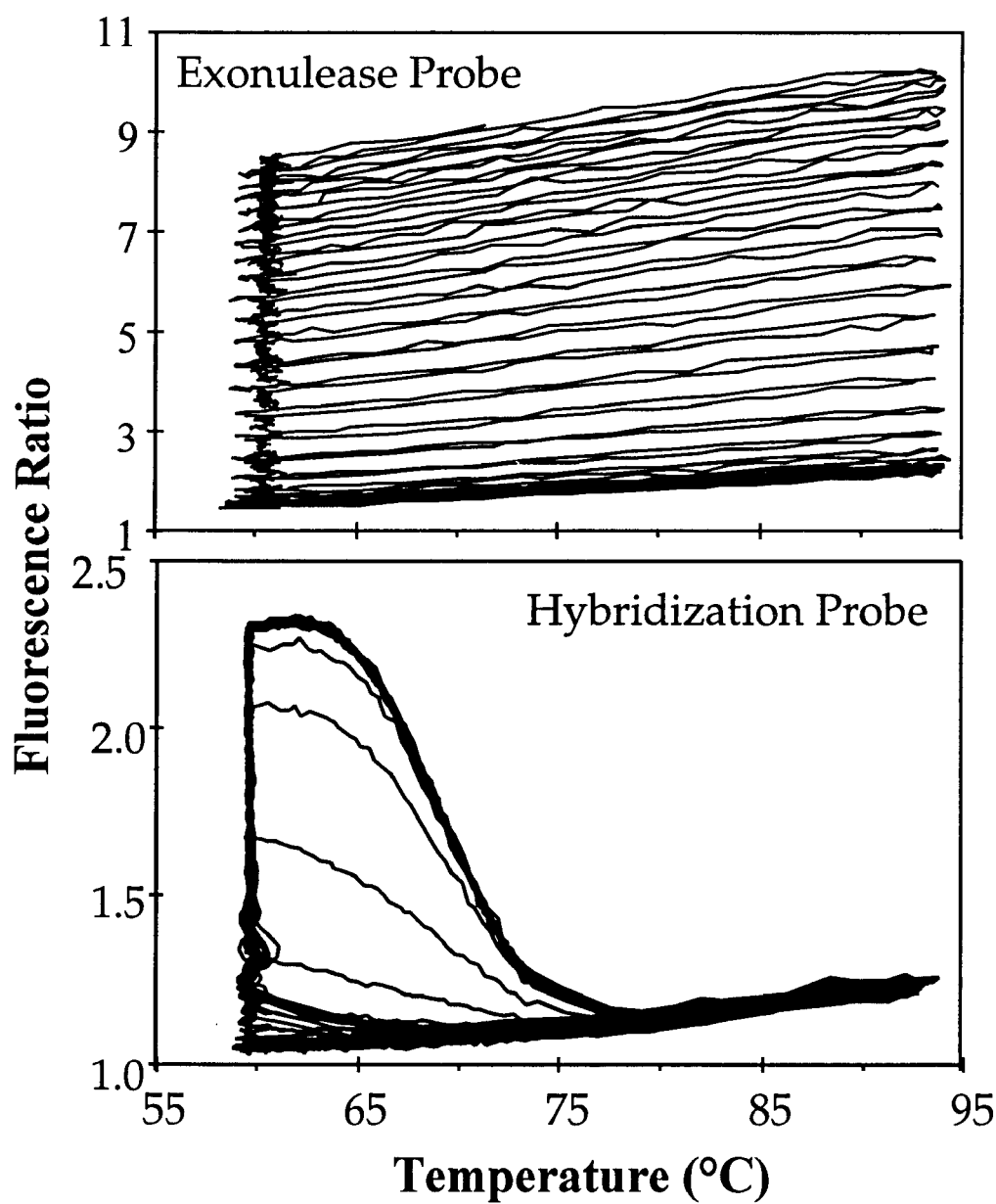
FIG. 2 shows fluorescence vs. temperature plots, illustrating the temperature dependence of the fluorescence from hybridization (bottom graph) and exonuclease (top graph) probes. These plots were generated by monitoring a single sample every 200 msec during PCR temperature cycling (Wittwer et al., *BioTechniques* 22:130–138 (1997)). In the annealing/extension phase, the hybridization probes hybridize to single stranded product and the fluorescence ratio (in this case, Cy5/fluorescein) increases. During heating to denaturation, the probes dissociate around 70–75° C., returning the fluorescence ratio to background levels. In contrast, exonuclease probes do not show this temperature dependence. As expected, fluorescence vs. temperature plots with exonuclease probes show only a linear dependence of fluorescence with temperature.

Probe melting temperature is dependent upon external factors (salt concentration and pH) and intrinsic factors (concentration, duplex length, GC content and nearest neighbor interactions) (Wetmur, *Crit. Rev. Biochem. Mol. Biol.* 26:227–259 (1991); Wetmur,. In: Meyers, R A, ed. Molecular Biology and Biotechnology, VCH, New York, pp. 605–608 (1995); Brown et al. *J Mol. Biol.* 212:437–440 (1990); Gaffney et al., *Biochemistry* 28:5881–5889 (1989)). Mismatches between the oligonucleotide probe and DNA target cause a decrease in the melting temperature of the duplex (Guo et al., *Nat. Biotechnol.* 15:331–335 (1997); Wallace et al., *Nucleic Acids Res.* 6:3543–3557 (1979)). Depending on the type of mismatch, varying degrees of destabilization occur. Mismatches that are relatively stable, for instance G-T mismatches, have melting temperature shifts of 2–3° C. (Bernard et al., *Anal. Biochem.* 255:101–107 (1998)) (see FIG. 1 for an illustrative example), while less stable C-A mismatches have 8–10° C. melting temperature shifts (Lay et al., *Clin. Chem.* 43:2262–2267 (1997); Bernard et al., *Am. J. Pathol.* 153:1055–1061 (1998)). Mismatch position and the number of mismatches also affect melting temperature (Wallace et al. (1979)). Accordingly, the percent identity of the hybridization probes to their target complementary sequence directly impacts the temperature at which the hybridization probe will separate (melt) from the complementary strand. The greater the difference between the probe and the target complementary sequence the lower the temperature needed to separate the hybridizing strands. Therefore, an oligonucleotide probe identical in sequence to the complementary wild type sequence will dissociate from the locus containing a mutation at a lower temperature than it will from the wild type locus. The use of fluorescently labeled hybridization probes enables dynamic monitoring of fluorescence as the temperature of the sample is raised and the melting curve for the hybridization probe is determined (see FIG. 2 for an illustrative example). The generated melting curve is then compared to the known melting curve for the normal, mutant or polymorphic sequence to determine the sequence of the target nucleic acid locus.

Accordingly, the present invention provides methods for analyzing a nucleic acid sample. As used herein, "nucleic acid" may refer to either DNA or RNA, or molecules which contain both deoxy- and ribonucleotides. By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included, having modifications which are well known in the art. Modifications of the ribose-phosphate backbone may be done to facilitate the addition of additional moieties such as labels, or to increase the stability and half-life of such molecules in various environments. Particularly preferred are peptide nucleic acids (PNA) which includes peptide nucleic acid analogs. The backbones of these are substantially non-ionic under neutral conditions, in contrast to the highly charged phosphodiester backbone of naturally occurring nucleic acids.

Nucleic acid samples may be from any source. In a preferred embodiment, the nucleic acid sample is a PCR product, as further described below. In another preferred embodiment, the nucleic acid sample is an LCR product.

Preferably, the nucleic acid sample has multiple loci. By "locus" herein is meant a position or location in the linear sequence of the nucleic acid which corresponds to the linear position in the genome of an organism of which a variation results in a variant hereditary character or phenotype in said organism. Such sequence variation may be a nucleotide substitution, insertion or deletion as compared with the wild-type sequence. In a preferred embodiment, the nucleic acid sample has at least two loci. In another preferred embodiment, the nucleic acid sample has at least three loci.

The wild type and variant sequences of a locus are herein referred to as "allelic sequences". In a preferred embodiment, a locus has at least two allelic sequences. In a preferred embodiment, a locus has at least three allelic sequences. In some embodiments of the invention, a locus has four, five, six, seven, eight, nine, ten or more allelic sequences. The only limitation to the number of allelic sequences that can be analyzed at a locus is the ability to distinguish the emission colors associated with the probes and to distinguish the Tm of all probes having the same associated emission color. As described below, three probes, each associated with a different emission color, can be used to determine the presence of 13 different allelic sequences at a single locus.

In a preferred embodiment, pairs of oligonucleotide probes are combined with the nucleic acid sample. By "probe" herein is meant a nucleic acid which hybridizes with specificity to a segment of a nucleic acid sample. Preferably, the probe pairs hybridize within a segment of a nucleic acid sample comprising a locus. In this embodiment, at least one probe hybridizes with a segment of the nucleic acid sample comprising two or more allelic sequences, such a probe being sometimes referred to as an "allelic probe" or an "allele specific probe". It is understood that either one or both probes of a probe pair can be an allelic probe.

In a preferred embodiment, one member of a probe pair is labeled with a FRET donor, while the other member of the probe pair is labeled with a FRET acceptor. As described in the background, several fluorophore combinations are known that may be used in the present invention, including phycoerythrin as the donor and Cy7 as the acceptor, and fluorescein as the donor in combination with any one of Cy5, Cy5.5, IRD 700, LC Red 640 and LC Red 705 as the acceptor. It is understood that any functional FRET donor/acceptor combination may be used in the invention. The only limitation is that the emission from each of the different FRET acceptors used must be distinguishable from the others.

Labeled probes can be constructed following the disclosures of, for example, Wittwer et al., *BioTechniques* 22:130–138, 1997; Lay and Wittwer, *Clin. Chem.* 43:2262–2267, 1997; and Bernard Pset al., *Anal. Biochem.* 255:101–107, 1998. Each of these disclosures is incorporated herein in its entirely.

In one embodiment, a member of one probe pair is also a member of a different probe pair. The FRET donor/acceptor combination may be different for the two different pairs. Alternatively, the possible Tm's of the first probe pair are distinguishable from the possible Tm's of the other probe pair, as more fully described below. In a preferred embodiment, a probe is labeled with two FRET donors, two FRET acceptors, or a FRET donor and a FRET acceptor. In this embodiment, the probe is a member of a first probe pair with one probe and a second probe pair with a different probe.

In a preferred embodiment, each of the members of a probe pair are capable of hybridizing in proximity to each other within a segment of the nucleic acid sample having at least one locus. In this embodiment, at least one of the probes is an allelic probe, hybridizing with at least one segment of the nucleic acid sample in which at least two allelic sequences are possible. Of course, the probe may hybridize with a segment having three, four, five, up to 10, up to 15 or more possible allelic sequences. Preferably, one of the probes of a probe pair is a "non-allelic probe", hybridizing with a segment of the nucleic acid sample which has no allelic sequences. Alternatively, both probes of a probe pair are allelic probes. In this alternative embodiment, the Tm of the probe pair should be distinguishable for each allelic sequence possible in the segment of the nucleic acid sample with which the pair hybridizes, as more fully discussed below.

In a preferred embodiment, two, three, four, five or more pairs of probes are used. In this embodiment, preferably at least one of the probe pairs comprise a FRET acceptor which has a different emission spectrum from the FRET acceptor of at least one of the other probe pairs. Alternatively, when at least three probe pairs are used, the FRET acceptor of each of a first probe pair, a second probe pair and a third probe pair has a different emission spectrum from the FRET acceptor of the other two. In an embodiment in which two or more probe pairs are used and two or more probe pairs comprise a FRET acceptor having the same emission spectrum, probe pairs comprising FRET acceptors having the same emission spectrum are preferably distinguishable by Tm. That is, the Tm of each probe pair for each allelic sequence with which the probe pair hybridizes is different from each Tm for each allelic sequence with which the other probe pair(s) comprising a FRET acceptor having the same emission spectrum hybridizes. Preferably in this case, it is the dissociation of the allelic probe which determines the Tm for each probe pair. In this way, probe pairs having similar FRET acceptors provide information regarding the presence or absence of a specific allelic sequence.

In a preferred embodiment, when the two members of a probe pair hybridize with the nucleic acid sample, the proximity of said probe pairs is sufficient to allow fluorescence resonance energy transfer (FRET) between the FRET donor and FRET acceptor of the pair. In this way, emission of fluorescence in the spectrum of a given FRET acceptor indicates that both members of the probe pairs comprising that FRET acceptor are hybridized to the nucleic acid sample.

In a preferred embodiment, the nucleic acid sample is the product of one or more PCR reactions. In another embodiment, the nucleic acid sample is the product of one or more LCR reactions.

In an alternative preferred embodiment, the nucleic acid sample is contacted with at least two or at least three PCR primer pairs. Preferably the nucleic acid sample comprises multiple loci, preferably at least two loci, or at least three loci. In a preferred embodiment, each PCR primer pair is specific for one locus of the nucleic acid sample. Preferably, the nucleic acid sample is contacted with the PCR primer pairs under conditions which allow formation of a linear amplification product for each PCR primer. PCR methods are well known in the art.

In a preferred embodiment, each amplification product formed as described above contains one of at least two, or at least three, or at least four, or five, or six, or seven, or eight, or nine, or ten, up to 15 or more allelic sequences which may be present at each locus within the amplification product.

In a preferred embodiment, each amplification product described above comprises at least one member of a FRET acceptor and FRET donor pair.

In a preferred embodiment, each loci specific amplification product is contacted with FRET labeled oligonucleotide probes. Preferably, each FRET probe hybridizes with the amplification product at a segment encompassing a specific locus in the amplification product. Preferably, each FRET probe has a sequence complementary to one allelic sequence which may be present at that specific locus. By "complementary" herein is meant a perfect match of base pairing (e.g., G+C; A+T or U) when two nucleic acids are hybridized. Preferably, each FRET probe forms a hybridization product with each of the allelic sequences at the same locus, wherein the hybridization product with each of the allelic sequences with which it is not complementary contains one or more mismatches, insertions or deletions as compared with the FRET probe and its complementary allelic sequence. Preferably, the mismatches, insertions or deletions result in differential Tm from at least two, preferably all possible allele at that locus.

In a preferred embodiment, each of the FRET probes described above contains a member of a FRET donor and acceptor pair that matches with the FRET donor or FRET acceptor contained in the amplification product with which it hybridizes. That is, when one of the probe and the amplification product contains a FRET donor, the other contains a FRET acceptor. In one embodiment, the FRET acceptor for a first FRET donor and FRET acceptor pair associated with one of the FRET probes has a different emission spectrum from at least one FRET acceptor associated with a second FRET probe. In another embodiment, each of the FRET acceptors associated with at least three FRET probes has a different emission spectrum from at least two different FRET acceptors associated with the other FRET probes. In a preferred embodiment, a first FRET probe having the same FRET acceptor associated with it as a second FRET probe will have, for each allelic sequence with which it hybridizes, a different Tm from each Tm for each allelic sequence with which the second probe hybridizes.

In a preferred embodiment, PCR primer sequences and FRET probe sequences are chosen such that, upon hybridization of a FRET probe with an amplification product, the FRET donor and FRET acceptor for each pair are in close proximity so as to allow fluorescence resonance energy transfer between the FRET donor and FRET acceptor. The design of such probes and primers is well within the skill of the ordinary artisan.

Devices for measuring fluorescence emission are known in the art. A device for measuring FRET acceptor emission at two different wavelengths at varying temperatures is also commercially available (i.e., LightCycler™). Devices for simultaneously detecting FRET acceptor emission at more than two wavelengths at varying temperatures are described below.

In a preferred embodiment of the invention, the emission of each FRET acceptor is measured at a different wavelength spectrum, preferably around its maximum emission wavelength, at a first temperature. This measurement is then repeated at a second temperature. In a preferred embodiment, such measurements are made repeatedly, preferably over a range of progressively increasing temperatures. Preferably, the first measurement is made at a temperature low enough to ensure that each of the probes is hybridized. Generally, this temperature will be at least 20° C., preferably at least 35–40° C. Emission measurements are made at subsequently higher temperatures. Eventually, as the temperature is increased, a probe will dissociate (melt) from the nucleic acid to which it is hybridized. This dissociation results in disruption of the FRET donor/acceptor association, which is seen as an abrupt drop in FRET acceptor emission. Dissociation temperatures of hybridized oligonucleotides generally do not exceed 95° C., preferably they do not exceed 80° C.

In a preferred embodiment, FRET acceptor emission measurements are made every 50 to 10,000 msec, more preferably, every 100 to 1,000 msec, most preferably every 100–200 msec. In a preferred embodiment, the temperature is varied by 0.01° C. per second to 5° C. per second, more preferably by 0.5° C. per second to 1° C. Preferably, the temperature is varied by at least 0.5° C. per second.

As used herein, "Tm" means the lowest temperature at which a probe associated with a FRET acceptor typically dissociates from the nucleic acid to which it is hybridized. By "probe associated with a FRET acceptor" and grammatical equivalents thereof is meant the FRET acceptor is contained by either a FRET probe or the amplification product with which it hybridizes, or by a probe pair member or the other member of the pair. In the case of oligonucleotide probe pairs wherein one member of the pair comprises a FRET donor and the other member of the pair comprises a FRET acceptor, Tm is the lowest temperature at which either member of the pair typically dissociates from the nucleic acid sample to which both members of the pair are hybridized. In a preferred embodiment, Tm is determined by dissociation of an allelic probe. In the case of amplification products comprising at least one member of a FRET donor and FRET acceptor pair, Tm is the lowest temperature at which a FRET probe hybridized to the amplification product typically dissociates therefrom.

Figure 3:
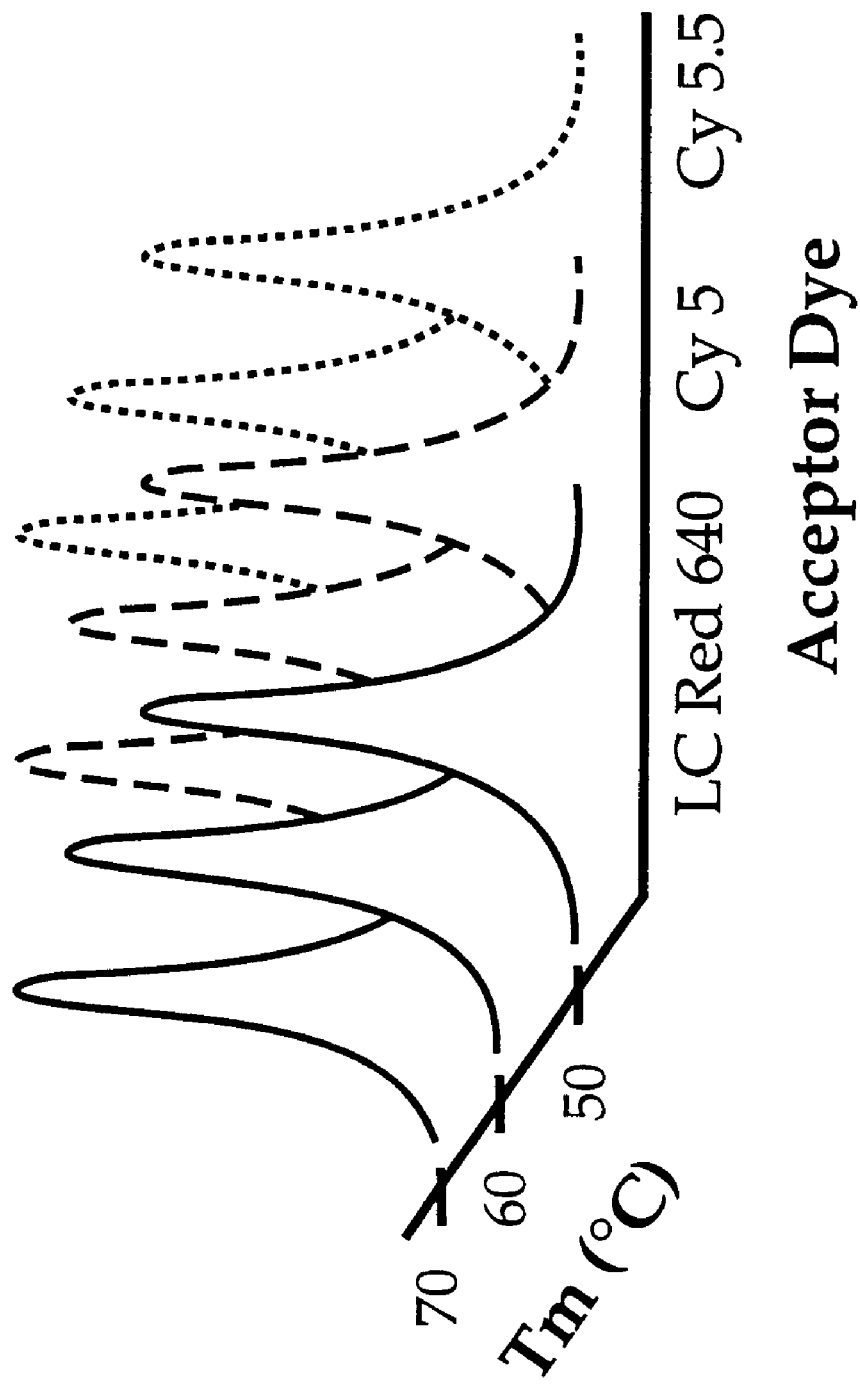
FIG. 3 illustrates that both color and Tm can be used simultaneously for multiplexing, creating a 2-dimensional matrix. Nine different products could be identified by 3 colors and 3 Tms. In general, the degree of multiplexing possible is the product of the number of colors used and the number of Tms distinguished.

The Tm of a probe is indicative of the allelic sequence to which it is hybridized. By designing a probe specific to a mutation locus, genotyping by melting curve analysis in real time is possible. Mismatch position and the number of mismatches also affect Tm and can be used to enhance polymorphism discrimination. Probes associated with the same FRET acceptor can be distinguished on the basis of Tm. Single color hybridization probes can identify multiple mutations under a probe and detect unexpected polymorphisms. By monitoring fluorescence continuously as the temperature is changed, probe melting curves can be obtained. These melting curves can be considered "dynamic dot blots", where the extent of hybridization is monitored at multiple temperatures. When fluorescence is acquired as the temperature is raised through the Tm of the probes, the probes sequentially melt from their target. When plotted against temperature, this change in fluorescence identifies each target by its Tm, making multiplexing possible. As mentioned above, number of targets that can be identified is essentially the product of the number of colors that can be detected and the number of Tm's that can be differentiated (see FIG. 3 for an illustration of this phenomenon).

In a preferred embodiment, fluorescence emission is monitored continuously through repeated cycles during PCR. If fluorescence is monitored continuously within each cycle during temperature transitions, the hybridization characteristics of PCR products and probes can be determined. With double stranded DNA (dsDNA) specific dyes, the product melting temperature (Tm) can be used to identify the products amplified. The dsDNA dyes bind only to double stranded DNA and emit fluorescence differentially when bound from when not bound. Dyes like ethidium bromide or SYBR Green I can be used in any amplification and are inexpensive. Although not sequence specific, product specificity can be increased by analysis of melting curves, as described above for probes, or by acquiring fluorescence at a high temperature where nonspecific products have melted. However, multiplexing by color is not possible. In a preferred embodiment, SYBR Green I is used to determine the hybridization characteristics of PCR products continuously through repeated cycles during PCR.

In addition, the melting of hybridization probes can be continuously monitored by resonance energy transfer, as described above. Probe melting occurs at a characteristic temperature that can be exploited for product identification, quantification and mutation detection.

Figure 6:
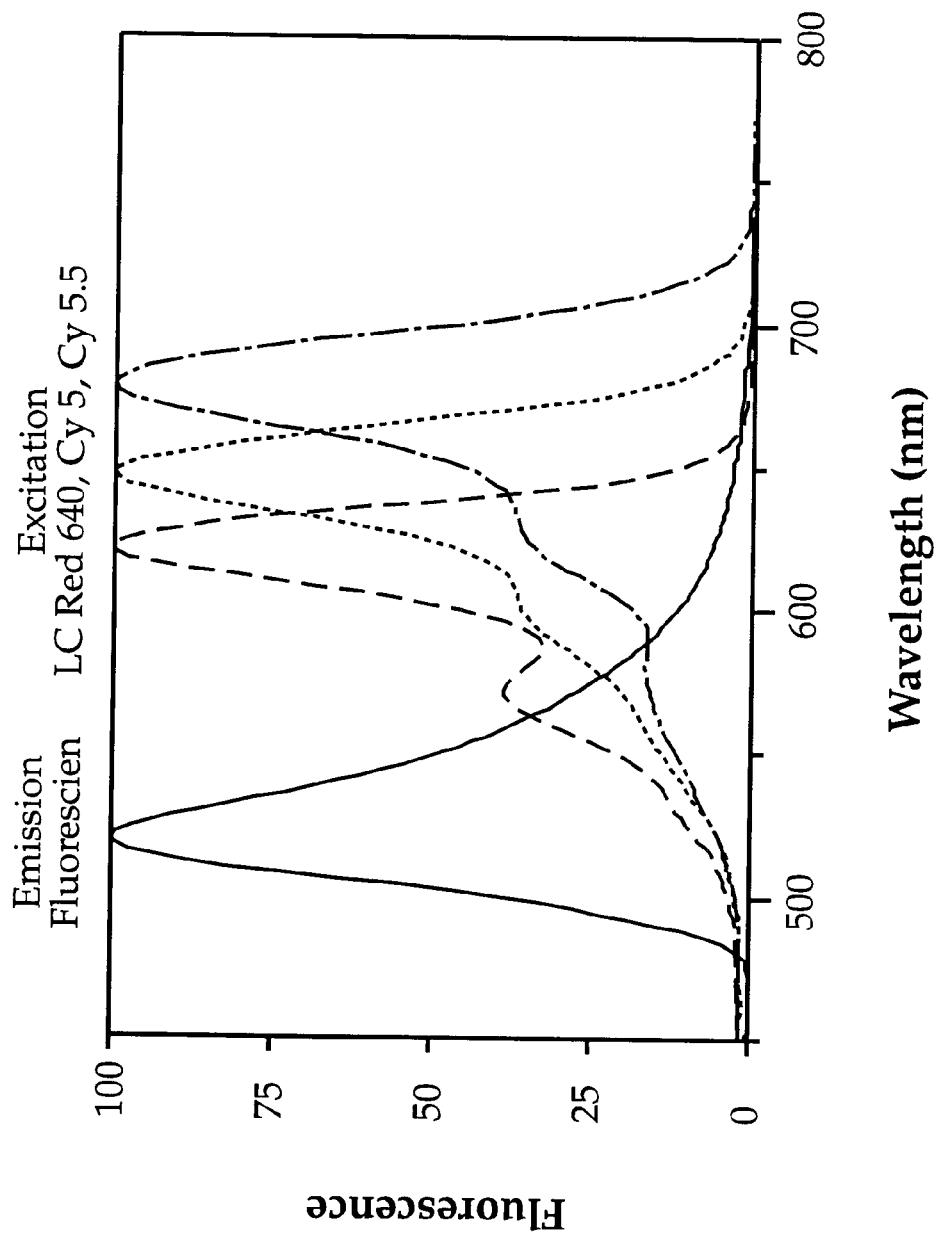
FIG. 6 shows the emission wavelengths of LC Red 640, Cy5, and Cy5.5.
Figure 7:
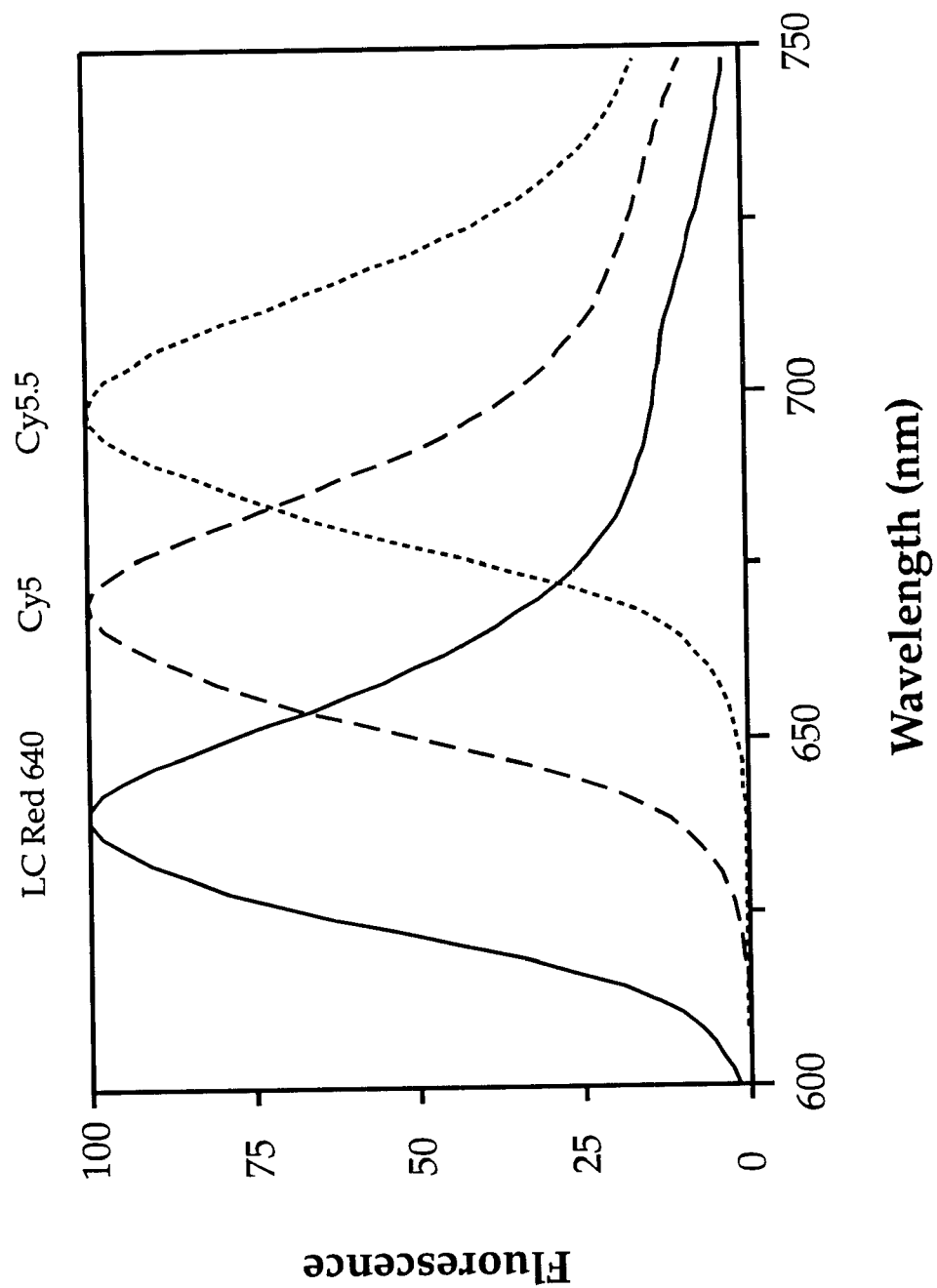
FIG. 7 shows the emission wavelengths of fluorescein and the excitation wavelengths of LC Red 640, Cy5, and Cy5.5 Although the spectral overlap is small, the molar absorption coefficient and absorption wavelengths of the acceptors are high. Spectral overlap, acceptor absorptivity, and acceptor wavelength all contribute to the overlap integral that determines energy transfer rates (Wu et al., *Anal. Biochem.* 218: 1–13 (1994)). Efficient resonance energy transfer occurs between fluorescein and LC Red 640, Cy5, and Cy5.5.

In a preferred embodiment, fluorescence emission measurements are corrected for spectral overlap between or among the different FRET acceptors (see FIGS. 6 and 7 for an illustration of spectral overlap). Fluorescence crosstalk between channels is compensated in software following methods developed for multicolor flow cytometry (e.g., Bagwell and Adams, *Ann. NY Acad. Sci.* 377:167–184, 1993.). However, color compensation algorithms developed for flow cytometry do not allow for changes in signal gains or temperature-dependent crossover effects. The change in crossover coefficients with temperature is not an issue when the temperature remains constant. However, with melting curve analysis, the temperature ranges from 40–90° C. and significant errors arise if the calibration data used to derive the crossover coefficients are obtained at a different temperature than the data to be evaluated.

Detailed methods for corrections for spectral overlap are found in U.S. patent application Ser. No. 09/374,422, filed Aug. 13, 1999, which is hereby incorporated in its entirety. Briefly, crossover constants are first obtained in a calibration run by acquiring the fluorescence of all individual fluorophores and an autofluorescence blank in each channel during a temperature ramp. The dependence of fluorescence on temperature can be approximated by a 3rd degree polynomial that is later used to evaluate crossover constants at any temperature. Once calibrated for a set of dyes, no further calibration is necessary. Using matrix notation for multiple channels, the compensated fluorescence (S) is equal to the inverse of the crossover constant matrix ($K^{-1}$) times the observed fluorescence (O) minus the autofluorescence (A), or $S=K^{-1}[O-A]$. Matrix functions are available in LabView, as well as other commercially available software. Further details of methods for spectral overlap compensation are found in the examples.

In a preferred embodiment, the emission measurements are made simultaneously at each wavelength. This allows for precise measurement of temporal coincidence of fluorescence emission. Because Tm is determined while temperature is varied over time, simultaneous measurements of emission provide the most accurate Tm calculation, allowing for maximum discrimination between Tm of probes from different alleles, in turn maximizing the number of allelic species that can be discriminated for a given FRET donor and FRET acceptor pair.

In another aspect of the invention, devices for continuous monitoring of fluorescence emission are provided. In general, these devices provide a source of electromagnetic radiation as an excitation source for fluorescent components in a chamber, which chamber has an optically transparent wall. The device generally uses various dichroic mirrors and band pass filters for isolating preferred spectra from the emissions of the fluorescent components Optical detectors are used to measure the isolated emission spectra. Embodiments of the invention provide novel solutions to problems of signal loss and complexity in the analysis of multiple emission signals of independent spectra from a single source.

Figure 4:
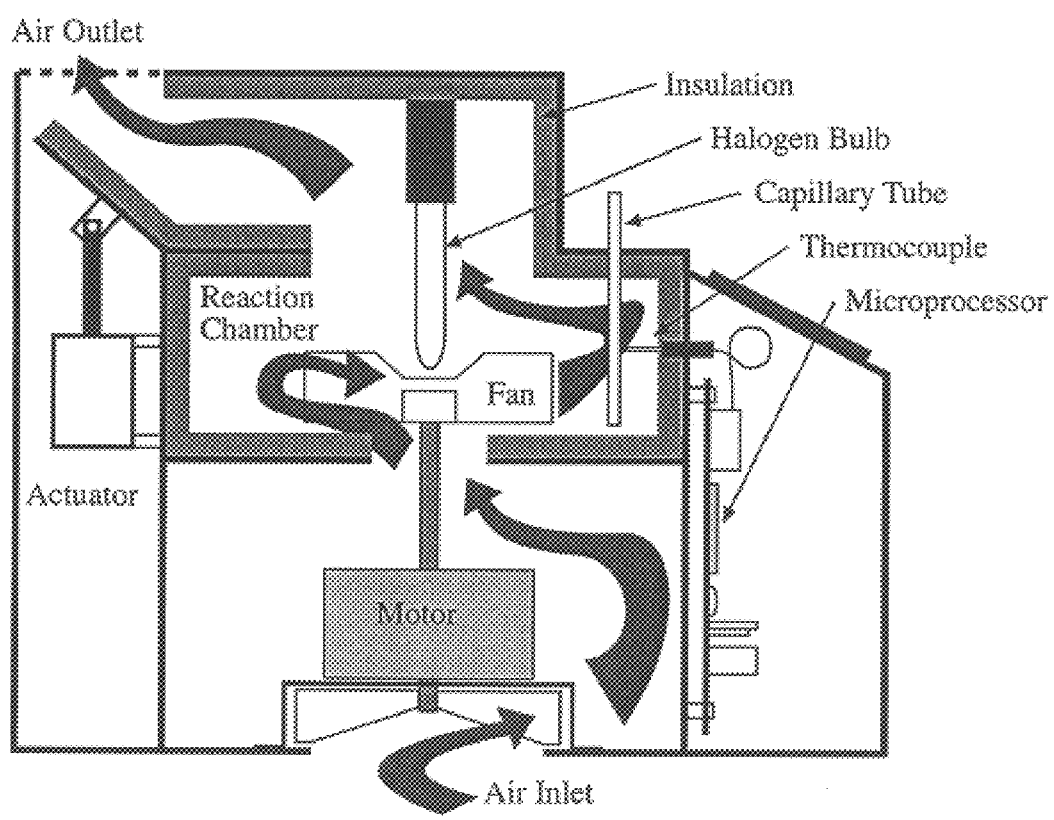
FIG. 4 shows a cut-away schematic of a rapid air thermal cycler, the RapidCycler™, made by Idaho Technology, which typically completes 30 PCR thermal cycles in 10–15 minutes.
Figure 5:
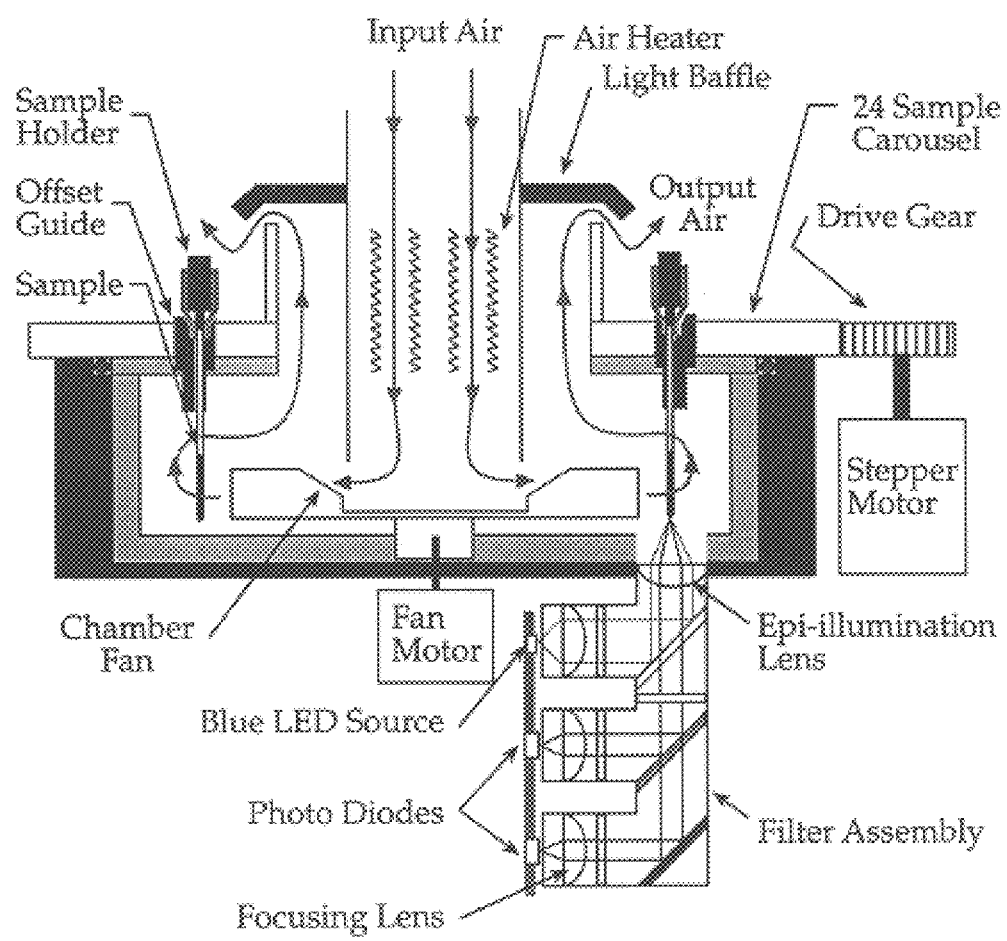
FIG. 5 shows the mechanical and optical design of the commercial LightCycler™, a rapid temperature cycler similar to the RapidCycler™, with a fluorimeter.

In a preferred embodiment, the invention provides a device for multichannel color analysis of a PCR or LCR reaction. The device comprises a chamber for holding a PCR or LCR reaction product. In a preferred embodiment the chamber comprises a PCR or LCR reaction chamber (e.g., FIG. 4, "reaction chamber", and its equivalent shown in FIG. 5). In one embodiment, the reaction chamber is a reaction chamber of a thermal cycling device, for example the device disclosed in U.S. Pat. No. 5,455,175, the disclosure of which is expressly incorporated herein. Such thermal cycling devices are designed for cycling samples repeatedly through a predetermined temperature-versus-time profile. Such apparatus are useful for processing PCR or LCR reactions.

In a preferred embodiment, the chamber comprises an optically transparent wall. The optically transparent wall may serve as both an inlet for electromagnetic radiation (e.g., light) to serve as an excitation source for components in the chamber. The optically transparent wall also serves as an egress from the chamber for electromagnetic emissions from components, particularly fluorescent components, in the chamber. In one embodiment, the optically transparent wall is a lense. In the latter embodiment, the lense may serve to focus electromagnetic radiation onto components in the chamber. The lense may also serve to focus emissions from the chamber toward a detector.

The device further comprises a source for providing electromagnetic energy. In a preferred embodiment, the source for providing electromagnetic energy, also referred to herein as an energy source, provides such energy to the optically transparent wall, through which the energy passes to impinge on a fluorophore to act as an excitation source. In a preferred embodiment, the energy source is positioned such that the energy provided travels in the same pathway as the fluorescent emissions which are detected by the device. This configuration is referred to as epifluorescence. In an alternative embodiment, the energy source is positioned to provide energy to the fluorophore from a different direction, preferably orthogonal to the pathway that detected fluorescent emissions travel. In the epifluorescence configuration, energy from the energy source can be reflected to the optically transparent wall by a dichroic mirror positioned in the detected emissions pathway, which dichroic mirror reflects wavelengths suitable for excitation of fluorophores within the chamber but allows wavelengths of emissions of interest from the chamber to pass to the detectors of the device.

Figure 8:
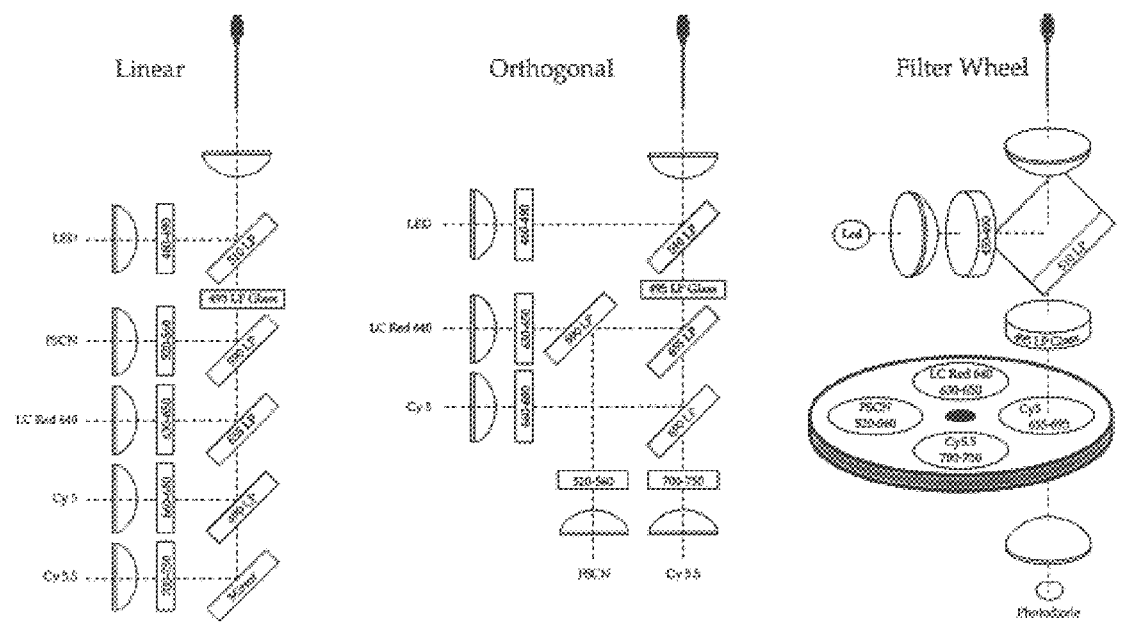
FIG. 8 shows three possible configurations for the energy source and emission detection components of a device of the invention. In the linear configuration, bandpass filters are shown vertically, dichroics diagonally, and the absorbance glass horizontally. Bandpasses and long pass (LP) cutoffs are shown in nm. The ideal spectral percentage that passes through the filters are indicated for fluorescein (FSCN), LC Red 640, Cy5, and Cy5.5. These spectral yields do not include reflection and absorption losses.

The device also comprises filters and, in some embodiments dichroic mirrors, to isolate a preferred spectrum of emission at a detector. Several embodiments representing different configurations of components are depicted in FIG. 8. In one embodiment, dichroic mirrors are positioned in linearly in the pathway of emissions from the chamber to be detected. In the linear configuration, long pass dichroic mirrors reflect emissions of increasing wavelength the farther they are positioned from the chamber. The mirror to reflect the longest wavelengths is not dichroic. Each mirror is positioned to reflect emissions to a band pass filter, on the other side of which is an optical detector positioned to detect the filtered emission. Preferably, the dichroic mirror closest to the chamber has a wavelength cutoff above the peak emission spectrum of the fluorophore having the shortest wavelength emission spectrum and bellow the peak emission spectrum of the fluorophore having the next shortest wavelength emission spectrum. Preferably, each subsequent dichroic mirror from the chamber has similar reflective characteristics such that it is optimized to reflect wavelengths of the peak emission spectrum of only a single fluorophore, taking into account the wavelengths reflected by mirrors earlier in the emission pathway, and not longer wavelength peak emission spectra of other fluorophores. Band pass filters preferably also pass wavelengths limited to the peak emission spectrum of a single fluorophore. This configuration requires alignment of a mirror and detector for each fluorophore to be detected. Also, the higher wavelengths must pass through progressively more mirrors, resulting in increasing losses from absorption and reflection. Because all colors are collected simultaneously, there is no time difference between acquisition of different colors (exact temporal coincidence).

In a preferred embodiment, approximately half of the band pass filters are positioned so that they are not coplanar with the others, preferably the filters within the first half are coplanar with each other and orthogonal to the filters in the other half. In this orthogonal configuration, long pass dichroic mirrors are positioned so that the first mirror to receive emission from the chamber has a cut off wavelength in the mid range of the spectra of emissions to be detected. The orthogonal design equalizes the number of optical elements that light in each channel must cross. The maximum number of elements and the pathlength of the longest wavelength dye are reduced, decreasing optical losses and alignment difficulty over the linear configuration. The paths emissions of at least two fluorophores cross in space; such a design for this type of device is not known in the art. There preferably is exact temporal coincidence.

In a preferred embodiment, the device comprises at least four band width filters, at least two of which are not coplanar. The filters are positioned to simultaneously or sequentially filter fluorescent emissions from the chamber to provide filtered multichannel fluorescence signals. In a preferred embodiment, the ban width filters limit the passage of to the emission spectrum of a single emission source. In a preferred embodiment, at least two of the band width filters are orthogonal to each other.

In a preferred embodiment, the device comprises at least three dichroic filters and two bandpass filters, wherein the bandpass filters are not coplanar. Preferably, the bandpass filters are orthogonal to each other. In this embodiment, the dichroic mirrors are positioned so that emissions passing through each band width filter intersect each other's path.

In yet another embodiment, multiple band pass filters are mounted in a wheel which, when rotated, sequentially aligns each filter in the pathway of emissions from the chamber to an optical detector. Dichroic mirrors for reflecting emission spectra are not need and the embodiment requires only a single detector. In one embodiment, a motor turns the wheel. Optical losses are minimized and only one detector needs to be aligned. However, detection of emission at each filtered spectrum is not simultaneous. In this embodiment, preferably the coefficient of variation between Tm's determined by the methods above for similar samples under similar conditions using the present embodiment as compared with continuous uninterrupted detection is less than 5%, more preferably less than 1%.

In each embodiment, the device comprises an optical detector positioned to receive the filtered emission signals. In a preferred embodiment, an optical detector is positioned in register with each band pass filter. Preferably, each optical detector detects the emission spectrum of a single fluorophore in the chamber.

While the foregoing embodiments are at present considered to be preferred, it is understood that numerous variations and modifications may be made therein by those skilled in the art and it is intended to cover in the appended claims all such variations and modifications as fall within the true spirit and scope of the invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Single base alterations within codons 112 and 158 of the apolipoprotein E (Apo E) gene account for the 3 common alleles ($\epsilon 2$, $\epsilon 3$ and $\epsilon 4$) and six phenotypes of Apo E (Mahley, Science 240, 622–630 (1988)). Oligonucleotide targets were synthesized to provide a model system for adjacent hybridization probe genotyping of Apo E alleles. By using artificial templates, the effects of target concentration, complementary strand competition, probe concentration, Mg++ concentration, and annealing conditions prior to melting curve analysis could be systematically studied irrespective of an amplification technique.

Materials and Methods

The human apolipoprotein E gene sequence (GenBank accession K00396) was used to design unlabeled target strands, unlabeled competitor (complementary) strands, and fluorescently labeled probes (Table I). All oligonucleotides were synthesized by standard phosphoramidite chemistry (Phannacia Biotech Gene Assembler Plus, Piscataway, N.J.). The 5'-labeled LC Red 640 (LightCycler Red 640) and LC Red 705 (LightCycler Red 705) acceptor probes were synthesized using a C6dT amino-modifier (Glen Research, Sterling, Va.) and an LC Red 705 phosphoramidite (Roche Molecular Biochemicals), respectively. The LC Red 640 N-hydroxysuccinimide ester (Roche Molecular Biochemicals) was manually conjugated to an equimolar concentration of oligonucleotide in 0.1 M borate buffer, pH 9.0. Incubation was performed for 2 hrs in the dark. Both acceptor probes were synthesized with a chemical phosphorylation reagent (Glen Research) at the 3' end. The 3'-fluorescein-labeled probes were synthesized on fluorescein-controlled pore glass cassettes (BioGenex, San Ramon, Calif.).

Table I. Oligonucleotides and Probes Used for Genotyping the Model Apolipoprotein E Locus.

Sequences for Genotyping Codon 112

$\epsilon 3$ Taget GGCGCAGGCCCGGCTGGCGCGGACATG-GAGGACGTGTGCGGCCGCCTG GTGCAGT$^a$ (SEQ ID NO: 1)

ϵ4 Target GGCGCAGGCCCGGCTGGGCGCGGA-
CATGGAGGAGG<u>ACGTGCGCGGCCGCCTGG</u>TG
CAGT$^a$ (SEQ ID NO: 2)
Fluorescent Probes CCAGGCGGCCGCACACG-
fluorescein (SEQ ID NO: 3) LC Red 705-
CCTCCATGTCCGCGCCCAGCCGGGCCTGCG
(SEQ ID NO: 4)

Sequences for Genotyping Codon 158

ϵ2 Target GCGGCTCCTGCCCGATOCCGATGACCT-
GCA<u>GAAGTGCCTGGCCAGTGTA</u> CCA$^a$ (SEQ ID NO: 5)
ϵ3 Target GCGGCTCCTGCCCGATGCCGATGACCT-
GCA<u>GAAGCGCCTGGCCAGTGTA</u>C CA$^a$ (SEQ ID NO: 6)
Fluorescent Probes ACACTGCCAGGCACTTC-
fluorescein (SEQ ID NO: 7) LC Red 640-
GCAGGTCATCGGCATCGGGCAGGAGCC (SEQ ID NO: 8).

A 5'-trityl group was retained during synthesis on the oligonucleotide target and competitor strands, the pre-conjugated LC Red 640 probe, and the fluorescein-labeled probes. Full-length sequences for all oligonucleotides and probes were purified by reverse-phase C18 high-pressure liquid chromatography (HPLC) using a 3.5 μM Waters Symmetry Column 4.6×1 50-mm (Waters, Milford, Mass.). The mobile phase consisted of 0.1 mol/L triethylammonium acetate, pH 7.0, and a 10 to 30% (fluorescein probe) or 10 to 80% (unlabeled oligonucleotides and LC Red 705 probe) gradient of acetonitrile (1 ml/minute). The eluate was monitored with tandem absorbance and fluorescence detectors (Waters 486 and 474, Milford, Mass.). For probes, fractions with coincident $A_{260}$ and fluorescence peaks were collected. Final detritylation was performed on a Polypack column (Glen Research, Sterling, Va.) and products were eluted with 50% acetonitrile.

The oligonucleotides and probes were vacuum dried, resuspended in 1 mM Tris-HCl, 0.1 mM EDTA, pH 8.0 and quantified. Unlabeled oligonuclueotides with $A_{260}/A_{280}$ values between 1.6 and 1.8 were used. The concentration ratio of fluorophore to oligonucleotide was calculated for each probe (Morrison, in Nonisotopic DNA Probe Techniques, Academic Press, San Diego, pp. 311–352 (1993)). Probes with ratios outside 0.9 to 1.1 were further purified on a denaturing 15% polyacrylamide gel containing 7 M urea followed by HPLC to remove the urea. A 3'-fluorescein labeled 17-mer probe was used at each codon for genotyping (FIG. 9). Although these probes were different in sequence, both formed an A:C mismatch flanked by C:G pairs when hybridized to the non-complementary target (Table I). The mismatch in both duplexes was positioned 5 base pairs in from the 3'-end of the probe.

Genotyping at each site was optimized for reagent concentrations and annealing conditions prior to melting curve analysis. Concentrations of $MgCl_2$, target strand, competitor strand, and fluorescein probe were varied. The $MgCl_2$ concentrations were varied from 1–5 mM. The concentrations of target oligonucleotides were varied from 0.05–0.2 μM and competitor oligonucleotides were at an equimolar concentration to the target strand. Fluorescein-labeled probes were varied from 0.1–0.2 μM. Each 10 μL reaction also contained 50 mM Tris, pH 8.5 (25° C.), 250 μg/ml bovine serum albumin and 0.2 μM of the acceptor probe (LC Red 640 or LC Red 705). FIG. 10 shows the different temperature conditions used for probe annealing prior to genotyping. Heterozygous samples were used to determine optimal conditions for genotyping, assessed as similar shaped Gaussian curves and equivalent peak areas.

A single temperature protocol and common reagents were necessary for multiplex genotyping. The reagents used were 1 mM $MgCl_2$, 0.05 μM target oligonucleotides for each site, 0.2 μM acceptor probe at each site, 0.1 μM fluorescein labeled probe spanning codon 112 and 0.2 μM fluorescein labeled probe spanning codon 158. The temperature protocol for multiplex genotyping is given in FIG. 10C.

The samples were loaded into composite plastic/glass capillary cuvettes, capped, briefly centrifuged and loaded into a 32-sample carousel of a thermal cycler with 3-color fluorescence monitoring capability (LightCycler™, Roche Molecular Biochemicals). Twelve samples were included in each melting curve analysis run. During the slow heating (0.1° C./s) phase of the genotyping protocol, fluorescence was continuously monitored with 100 ms acquisitions. The fluorescence of fluorescein, LC Red 640 and LC Red 705 was acquired in exact temporal coincidence using a linear arrangement of dichroic bandpass filters.

Color compensation for spectral overlap of fluorescent dyes was modified from flow cytometry techniques (Bagwell et al., (1993)). Custom analysis software was written in Lab View (National Instruments, Austin, Tex.). In summary, a calibration run of each pure fluorescent dye and autofluorescence control was first obtained with fluorescence values acquired in each channel. Signal crossover constants were calculated from these values and used to convert observed fluorescence (o) to actual signal fluorescence (s) by matrix algebra.

Several modifications to the color compensation algorithms developed for flow cytometry were necessary for use on genotyping data. Following the notation given in Bagwell et al. (1993), and eliminating the acquisition of multiple events (relevant to-flow cytometry but not to solution fluorescence), the crossover constants are:

$$k(i, jj) = \frac{o(i, jj) - a(j)}{\sum_{n=1}^{N} [o(i, n) - a(n)]}$$

where: k(i, jj)=crossover constant of dye i in channel j
o(i, j)=observed signal of dye i in channel j
a(j)=autofluorescence in channel j
n=channel index
N=maximum channel Preliminary experiments showed that the fluorescence of some of the dyes, and the crossover constants of some dye/channel combinations, were temperature dependent over the desired range of analysis (40–95° C.). Therefore, calibration runs were obtained by acquiring fluorescence continuously during a 0.2° C./s temperature ramp from 40 to 95° C. The temperature vs. fluorescence curves were nearly linear, but were better approximated by $3^{rd}$ degree polynomials. The $3^{rd}$ degree polynomial coefficients for the temperature vs. fluorescence curves of each of the dye/channel combinations and the autofluorescence controls of each channel were stored for temperature interpolation.

To color compensate fluorescence data, the temperature of each acquisition was used to interpolate temperature-specific fluorescence from the calibration curves. These values were then adjusted for any change in electronic gain between the calibration and data run as follows:

$$o(i,j)=[w(i,j)T^3+x(i,j)T^2+y(i,j)T+z(i,j)][G_D(j)/G_C(j)]$$
$$a(j)=[m(j)T^2+p(j)T+q(j)][G_D(j)/G_C(j)]$$

where: w(i, j), x(i, j), y(i, j), and z(i, j) are $3^{rd}$ degree polynomial coefficients for the temperature vs. fluorescence curve of dye i in channel j m(j), n(j), p(j), and q(j) are $3^{rd}$ degree polynomial coefficients for the temperature vs. fluorescence autofluorescence curve in channel j T=acquisition temperature $G_D$ (j)=gain of channel j during the data run $G_D$(j)=gain of channel j during the calibration run The actual signal fluorescence of each dye is calculated by the matrix equation:

$$S = K^{-1}[O-A]$$

where: S=actual signal fluorescence of each dye

K=crossover constant of each dye in each channel

O=observed fluorescence in each channel

A=observed autofluorescence in each channel

If temperature correction is desired as well as color compensation, the calibration data is color compensated by the above procedure and the temperature vs. actual signal fluorescence curves are fit to 3rd degree polynomials and the coefficients stored for temperature interpolation. The data run is color compensated and the fluorescence of each dye during each acquisition is temperature corrected as follows:

$$s_{TC} = s[s_C(T_S)/s_C(T_D)]$$

where: s=temperature corrected signal fluorescence s=signal fluorescence $s_C(T_S)$=interpolated signal fluorescence from the calibration run at a standard temperature (selected by the user)

$s_C(T_D)$=interpolated signal fluorescence from the calibration run at the data acquisition temperature An example of the results of color compensation and temperature correction is shown in FIG. 11.

Results

The quality of melting curve analysis depends not only on the melting protocol, but also on the annealing conditions before the melting curve acquisition. FIG. 10 shows that slow and stepwise temperature annealing protocols result in more symmetrical heterozygous melting peaks than annealing using a single rapid temperature transition. This result was observed even though the total annealing times were approximately the same (compare FIGS. 10A, B, and C). Table II shows a comparison of the Tm shifts created by the same mismatch at the 2 sites using different MgCl₂ concentrations. The mismatches destabilize the probe/target duplexes at each site by approximately the same amount (<1° C. difference). Furthermore, the ΔTm between the matched and mismatched duplexes was increased with a higher MgCl₂ concentration, while increasing the fluorescein probe concentration increased the Tms of both duplexes without affecting the ΔTm (data not shown).

TABLE II

Empirical Melting Temperatures for Fuorescein Probe/Target Duplexes

| [MgCl] | Codon | Probe:Target Base Pair Genotyping | Duplex Tm | ΔTm |
|---|---|---|---|---|
| 1 mM | 112 | A:T | 70.0 | 5.9 |
|  |  | A:C | 64.1 |  |
|  | 158 | A:T | 62.4 | 6.6 |
|  |  | A:C | 55.8 |  |

TABLE II-continued

Empirical Melting Temperatures for Fuorescein Probe/Target Duplexes

| [MgCl] | Codon | Probe:Target Base Pair Genotyping | Duplex Tm | ΔTm |
|---|---|---|---|---|
| 3 mM | 112 | A:T | 7.12 | 6.5 |
|  |  | A:C | 64.7 |  |
|  | 158 | A:T | 64.2 | 7.0 |
|  |  | A:C | 57.2 |  |

The clear resolution of a heterozygote at codon 112 (spanned by an 82% GC probe) was dependent on a low MgCl₂ concentration (FIG. 12A vs. 12B). In contrast, heterozygote genotyping at codon 158 (spanned by a 59% GC probe) was more symmetric with a higher Mg++ concentration and a low target concentration (FIG. 12C vs. 12D).

Genotyping from a double stranded product (i.e., equal concentrations of target and complementary strand) is illustrated in FIG. 13. In the presence of competitor (complementary strand), genotyping optimized to the same parameters shown in FIG. 12 but with a reduction in fluorescence signal to approximately 60% at each site.

FIG. 11 displays the effect of color compensation and temperature correction applied to a calibration run and to color multiplexing of the Apo E locus. The temperature dependence of LC Red 705 is substantial, whereas LC Red 640 fluorescence is almost constant with temperature (FIG. 11A). As expected, only the LC Red 705 calibration sample shows fluorescence after compensation (FIG. 11B) and the temperature dependence is removed after temperature correction (FIG. 11C). The original fluorescence vs. temperature traces for the LC Red 705 channel (codon 112) are complex and not interpretable because of fluorescence overlap from LC Red 640 (FIG. 11D). However, single temperature transitions are discerned after color compensation (FIG. 11E). After temperature correction (FIG. 11F), the baseline slope outside of the transition region is increased.

Multiplexing by color and Tm provides simultaneous identification of variants at codons 112 and 158 in a single tube within 10 minutes. FIG. 14 shows the uncompensated (A) and compensated (B) fluorescent melting peaks for genotyping codon 112. Without compensation, there is substantial bleed over from the LC Red 640 acceptor dye into the channel for monitoring the LC Red 705 acceptor dye. This results in apparent products with Tms of 55° C. and 62° C. However these additional peaks disappear after compensation, revealing the true homozygous genotypes at codon 112. All the genotypes for the 6 naturally occurring Apo E protein isoforms could be differentiated. In addition, the other 3 possible genotypes not normally found in human populations were constructed using synthesized templates and were correctly analyzed (data not shown).

Multiplex genotyping was optimal using low concentrations of both target and MgCl₂. Using the lower MgCl₂ concentration for genotyping codon 158 decreased the peak area of the mismatched duplex. Nevertheless, this resulting asymmetry in the heterozygous peaks could be partially compensated for by lowering the annealing target temperature (from 48° C. to 42° C.) before melting (FIG. 15).

Example 2

Exon 1 of the b-globin gene has over 50 mutations resulting in various hemoglobinopathies. Hemoglobin S, C, and E are common and are routinely screened. Hemoglobin C (Hb C) results from a G to A mutation in the first nucleotide of codon six while hemoglobin S (Hb S) arises by an A to T mutation in the second nucleotide of this codon. Hemoglobin E (Hb E) results from a G to A mutation in the first nucleotide of codon 26. The close proximity of these three mutations allowed us to design a probe system with discrimination of all genotypes by $T_m$ and two probe colors.
Materials and Methods The human b-globin gene sequence (GenBank Accession U01317) was used to design primers and probes for the amplification of a 214 bp segment containing exon 1 (FIG. 16). Due to high homology between b-globin and d-globin sequences, the primers (sense: GTCAGGGCAGAGC-CATCTA (SEQ ID NO: 9), antisense: GTTCTATTGGTCTCCTTAAAGGTG, SEQ ID NO: 10) were designed with 3' and additional mismatches to d-globin. Due to the close proximity of the hemoglobin mutations, a unique combination of probes were designed to detect Hb S, C, and E alleles. Two probe and LightCycler Red 705 (LC Red 705, Roche Molecular Biochemicals, Indianapolis, Ind.), as mutation detection probes. The third probe was a dual-labeled fluorescein donor probe which spans the distance between the mutation detection probes. When annealed, resonance energy is transferred from each fluorescein label to either the LC Red 640 or the LC Red 705 labeled probes. The codon 6 detection probe (CTCCTGTGGAGAAGTCTGC-LC Red 640, SEQ ID NO: 11) completely matched the Hb S allele anti-sense strand. The codon 26 probe (LCR 705-GTTGGTGGTAAGGCCCTGG-phosphate SEQ ID NO: 12) completely matched the Hb E allele anti-sense strand. Both the LC Red 640 and LC Red 705 probes were obtained from Idaho Technology Biochem (Salt Lake City, Utah). The fluorescein-labeled probe was labeled with two fluoresceins (F) attached to the 5' and 3' ends (F-GTTACT GCCCTGTGGGGCAAGGTGAACGTGGATGA-F, SEQ ID NO: 13) (Operon, Alameda, Calif.). Fifty-five blinded samples of human genomic DNA were randomly selected from samples submitted to Neo Gen Screening for sickle cell hemoglobinopathy screening. The DNA (80–130 ng) was prepared from blots on filter paper and had been previously genotyped by allele specific cleavage and gel electrophoresis.

PCR and melting curve analysis were preformed on the LightCycler™ (Roche Molecular Biochemicals, Indianapolis, Ind.). Asymmetric amplification of the antisense strand occurred in 10 mL of 50 mM Tris, pH 8.5 (25° C.), 3 mM MgCl$_2$, 500 mg/ml bovine serum albumin, 0.2 mM each deoxyribonucleoside triphosphate, 0.5 mM sense primer and 1.0 mM anti-sense primer, 1 U KlenTaq DNA polymerase (ABPeptides, St. Louis, Mo.), 0.2 mM LC Red 640 probe, 0.2 mM LC Red 705 probe, 0.4 mM dual fluorescein-labeled probe and 2.0 mL of human genomic DNA. The samples were thermally cycled 40 times with three temperature segments. The first segment was 94° C. for 0 sec at 20° C./sec for denaturation. A second segment of 63° C. for 30 sec at 20° C./sec allowed for both primer and probe annealing. A third temperature segment for extension consisted of a temperature ramp at 1° C./sec from 63 to 75° C. After amplification the temperature was raised to 94° C. for 5 sec, lowered to 35° C. at 1° C./sec, and held at 35° C. for 20 seconds. Melting curve profiles where obtained by raising the temperature to 80° C. at 0.1° C./sec while collecting fluorescence data continuously. Genotyping the samples by $T_m$ was accomplished after color compensation of each channel. $T_m$'s were determined by converting melting curves to –dF/dT derivative peaks and fitting the peaks to Gaussian curves (Lightcycler™ software, Roche Molecular Biochemicals).

Melting curve analysis of codon 6 (Hb S, Hb C), and codon 26 (Hb E) point mutations is shown in FIG. 17. Panels 17A–C show derivative plots that display "melting peaks" for the LC Red 640 labeled probe and Panel 2D displays results from the LC Red 705 probe. Panel 10A shows single peaks for both the homozygous Hb S ($T_m$=63.7° C., SD=0.18, n=25) and the wild type ($T_m$=56.4° C., SD=0.26, n=49) genotypes. Two melting peaks are present for the S-trait corresponding to each allele. Panel 10B shows the melting peaks for homozygous Hb C ($T_m$=50.9° C., SD=0.48, n=8). The C-trait has both the Hb C and wild type peaks. The genotype of a compound heterozygote, Hb S/C, is shown in panel 10C along with the corresponding Hb C and Hb S genotypes. Genotyping of the Hb E allele is shown in panel 10D. Single melting peaks are shown for homozygous Hb E ($T_m$=66.1° C., SD=0.13, n=3) and wild type ($T_m$=57.1° C., SD=0.20, n=52) genotypes, while the E-trait has two melting peaks corresponding to each allele. The codon 6 and codon 26 probes discriminated the ten most common hemoglobin genotypes in Exon 1. Homozygous samples for wild type (codon 6: n=21, codon 26: n=50), Hb S (n=1), Hb C (n=2), Hb E (n=1) as well as S-rait (n=23), C-trait (n=5) E-trait (n=2) and the compound heterozygotes Hb S/E (n=1), C/E (n=1), S/C (n=1) were correctly genotyped. The codon 6 probe sequence that showed the best resolution between the wild type, Hb S, and Hb C alleles was completely matched to the Hb S allele. Probes that matched either the wild type or Hb C alleles did not resolve all genotypes as effectively. The total time for amplification and genotyping of 32 samples was under an hour.

Example 3

Hybridization probe multiplexing by color and $T_m$ is used to analyze sequence variation at highly polymorphic HLA loci. Tm multiplexing with up to four fluorescent dyes (fluorescein, LC Red640, Cy5, and LC Red705) are used. A common fluorescein-labeled probe acts as the resonance energy transfer donor and does not contribute to the multiplexing of the acceptor dyes. Probe sets have been designed for the HLA-A and the HLA-DRB1 loci. Eight different sequence groups at HLA-A (index of heterozygosity=0.86) can be distinguished with 2 acceptor colors. Similarly, 13 HLA-DRB1 sequence groups (index of heterozygosity= 0.91) can be differentiated with 3 acceptor colors. Aligned sequences were obtained from the HLA Interest Group (www.anthonynolan.com/HIG) and allele frequencies taken from typing 1726 unrelated individuals of various racial backgrounds from Utah (Dr. Tom Fuller, consultant, personal communication). Highly polymorphic DNA which has been previously typed for HLA alleles is used to confirm results.

One of the hyper-variable regions in HLA-A is at codons 62–67 in exon 2 (FIG. 18). Variable bases ate indicated in bold type. Just upstream of this region is an area that is mostly conserved among the various HLA-A alleles. One fluorescein donor probe and two acceptor probes, one labeled with LC Red640 and one with LC Red705, are synthesized. (Lay MJ et al., Clin. Chem 43:2262–2267 (1997); Bernardet al., Am. J. Path, 153:1055–1061(1998); Bernardet al., Anal. Biochem. 273:221–228 (1999)), A 182 bp region flanking the probes will be amplified by rapid cycle PCR with primers GACAGCGACGCCGCGAGC (SEQ ID NO: 14) and GGGCCGGOGTCACTCACCG (SEQ ID NO: 15). These primers have 3'-mismatches with all Class I loci except for HLA-A, which provides for allele specific amplification (Wittmwer et al., Clin. Chem. 39:804–809 (1993)). The probes are included in the amplification mixture, PCR is performed and a melting curve is obtained at 0.1–0.2° C./sec.

The acceptor probes are designed to melt between 50–73° C. with all sequence groups (FIG. 19 and Table III). The donor probeserves as an anchor and remains annealed during the melting of the acceptor probes. Two-hundred previously-typed DNA samples (400 alleles) are tested (samples courtesy of Dr. Tom Fuller, consultant) With only the LC Red 640 probe, it is possible to distinguish all 8 HLA-A sequence groups. Heterozygotes in sequence groups that melt near each other are the most difficult to distinguish. The smallest predicted Tm difference is 1.3° C. between groups A and B. The addition of the LC Red705 probe unambiguously distinguishes all sequence groups. The probe Tms most useful in distinguishing between sequence groups are shown in bold type. The mean and variance of the actual Tms are compared to predicted values. Any disagreement between prior typing and LightCycler analysis are resolved by sequencing and repeat analysis.

TABLE III

Predicted Tms for 2 Probes at a HLA-A Variable Region

| Sequence Group | HLA-A Alleles | Frequency (%) | Predicted Probe Tm LCRed 640 | LCRed 705 |
|---|---|---|---|---|
| A | 0101–0103 0106 3601 | 15.2 | 71.6 | 63.3 |
| B | 3002–3006 3101 3103 3104 3201–3204 7401–7404 | 6.2 | 70.3 | 67.6 |
| C | 0301 0302 0304 0305 | 13.4 | 67.8 | 65.0 |
| D | 0201 0202–0207 0209–0219 24XX 16 additional 02XX | 27.2 | 66.1 | 72.3 |
| E | 2301–2305 2402–2406 8 additional 24XX | 11.1 | 61.6 | 62.5 |
| F | 2901–2903 7 additional 68XX | 3.6 | 58.9 | 59.6 |
| G | 2501 2503 2601–2606 2608–2612 3301–3305 | 7.2 | 56.8 | 57.8 |
| H | 2502 2613 6601 6602 6801–6802 | ~7 | 52.8 | 54.1 |
| | Total Estimated Frequency | 90.9 | | |

In a similar fashion, variation within the HLA-DRB1 region is assessed by color and Tm multiplexing. Codons 70–74 of exon 2 are hyper-variable and adjacent to a conserved region (FIG. 20). One donor probe and 3 acceptor probes are synthesized. A 193 bp region flanking the probes are amplified with primers AGCGGGTGCGGTTCCTGG (SEQ ID NO: 16) and CAACCCCGTAGTTGTGTCTG-CAGTAG (SEQ ID NO: 17) At least one of these primers is 3'-mismatched with all other DRB subclasses. It has been verified by sequencing that these primers specifically amplify only DRB1 alleles.

The acceptor probes are designed to melt under 70° C. (FIG. 21 and Table IV) Melting temperatures below 40° C. are difficult to obtain on the LightCycler and are not used for differentiation The donor probe is stabilized with a minor groove binder to increase its Tm (utyavinetal., *Nucl. Acids Res.* 28:655–661 (2000)). The same 200 previously typed samples are analyzed. Most of the sequence groups are identified with the LC Red 640- and Cy5-labeled probes, although the LC Red 705 probe is required for two groups. The smallest predicted Tm difference is 1.5° C. between groups I and J. Any disagreement between prior typing and LightCycler analysis is resolved by sequencing and repeat analysis. The smallest Tm difference that is reliably distinguished in heterozygotes is determined. This establishes the maximum number of sequences that can be distinguished by Tm multiplexing.

TABLE IV

Predicted Tms for 2 Probes at a HLA DRB1 Variable Region

| Sequence Group | DRB1 Alleles | Frequency (%) | Predicted Probe Tm LCRed 640 | Cy5 | LCRed 705 |
|---|---|---|---|---|---|
| A | 0101 0404 0405 0408 0410 1402 1406 | 15.8 | 69.5 | 59.0 | 23.8 |
| B | 0801 0802 0803 0804 | 4.1 | 61.2 | 45.7 | 28.3 |
| C | 1501 1502 1503 | 13.6 | 60.9 | 50.4 | 27.8 |
| D | 0401 | 6.4 | 60.1 | 43.6 | 35.3 |
| E | 0901 1401 1404 | 3.8 | 57.1 | 50.6 | 23.5 |
| F | 1001 | 0.9 | 54.5 | 46.9 | <20.0 |
| G | 11011 11012 11014 1305 16012 16022 | 7.5 | 54.1 | 68.1 | 24.1 |
| H | 0103 0402 1102 1103 1301 1302 1304 | 13.1 | 46.4 | 59.0 | 26.1 |
| I | 1303 | 1.2 | 37.4 | 58.2 | 36.3 |
| J | 11013 1201 1202 16011 16021 | 4.5 | 35.5 | 56.7 | <20.0 |
| K | 0301 0302 0303 0305 | 10.1 | 34.4 | <20.0 | 59.2 |
| L | 0403 0407 | 2.0 | 29.3 | 53.6 | 33.6 |
| M | 0701 | 8.2 | <20.0 | 46.9 | 58.0 |
| | Total Estimated Frequency | 92.0 | | | |

An additional dye that is spectrally separated from current hybridization probe acceptors is IRDye800(LI-COR, Lincoln, Nebr.). Primers labeled at the 5'-end are available from the company. Extension from the 3'-end can be blocked by either 3' mismatches or enzymatic addition of a ddNTP. The LC Red640 probe of FIG. 20 is replaced with an IRDye800 probe and the results compared. Finally, a 5-color (4-acceptor) probe set at HLA-DRB1 is produced by adding in a fifth probe (homologous to the DRb1-0103 allele) labeled with IRDye800.

Example 4

Tandem hybridization probes with equal Tm's (FIG. 22) are used to scan for mutations in a nucleic acid sample of known wild-type sequence. Multicolor hybridization probes are made such that each probe is labeled once or twice with one type of FRET donor or one type of FRET acceptor. Probes labeled twice are a member of a probe pair with two different probes. The probes are constructed such that, upon hybridization, probes with FRET acceptors are adjacent to probes with FRET donors, alternating along the length of the sample to which the probes hybridize. Single bases may separate the segments of the sample hybridized to the probes. In this way, a large region of a sample is analyzed for mutations. When the region is amplified, a mutation will decrease the observed Tm in either 1 or 2 FRET acceptor emission spectra. A mutation in a segment to which a FRET acceptor labeled probe hybridizes affects one emission spectrum, a mutation in a segment to which a FRET donor labeled probe hybridizes affects two emission spectra. Which channels are affected identifies the probe the mutation destabilizes. In some cases, the exact mutation may be identified by the Tm shift observed. If the individual probe length is about 30 bases, a region of 150 bases is screened with 5 probes using three different FRET acceptors. A region of 270 bases is scanned with 9 probes using five different FRET acceptors. Alternatively, the 1 base pair gap between probes is covered by a second, interdigitating probe set.

What is claimed is:

1. A method for analyzing a nucleic acid sample comprising three or more loci each having at least two different allelic sequences, said method comprising:

(a) combining at least a first, a second and a third pair of oligonucleotide probes with said nucleic acid, each of the members of said pairs being capable of hybridizing in proximity to each other to a segment of said nucleic acid comprising at least one of said three or more loci, wherein (i) the first member of each pair comprises a FRET donor and the second member comprises a FRET acceptor, wherein the FRET acceptor of the second member in said first pair has an emission spectrum which is different from the emission spectrum of the FRET acceptor of said second and third oligonucleotide probe pairs, (ii) when said second and third probe pairs have the same FRET acceptor, each of said second and third probe pairs has a different Tm from each other for each different allele within the nucleic acid segment to which each member hybridizes (iii) upon hybridization, the proximity of the members of a probe pair is sufficient to allow fluorescence resonance energy transfer between said FRET donor and said FRET acceptor, and (iv) at least one of said members of each pair has a sequence which results in the differential hybridization of that member with at least two different alleles which may be present at said loci;

(b) measuring the emission of each of said FRET acceptors at a first temperature; and (c) repeating said emission measurements at a second temperature; wherein the emission of said FRET acceptors at different temperatures provides an indication of the alleles present at said three or more loci.

2. The method of claim 1, wherein the FRET acceptor of each of the second members of each of a first, a second and a third probe pair has an emission spectrum which is different from the emission spectrum of the others.

3. The method of claim 1 or 2, wherein said nucleic acid sample is the product of one or more reactions selected from the group consisting of PCR, 3SR, SDA and RCA.

4. The method of claim 1 or 2, wherein at least one probe comprises two FRET acceptors, two FRET donors or a FRET acceptor and a FRET donor, and said probe is a member of two different probe pairs.

5. The method of claim 1 or 2, wherein steps (b) and (c) are repeated throughout a range of temperatures.

6. The method of claim 5, wherein said range is from at least 20° C. to at most 95° C.

7. The method of claim 5, wherein said emission measurements are repeated at least every 0.1 to 10 seconds.

8. The method of claim 7, wherein the temperature is varied at least 0.01 to 1° C. per second.

9. The method of claim 1 or 2, wherein said emission measurements at a particular temperature are simultaneous.

10. The method of claim 1 or 2, wherein at least one of said FRET acceptors is selected from the group consisting of LC Red 640, Cy 5, Cy 5.5 and LC Red 705.

11. The method of claim 1 or 2 wherein said emission measurements are corrected for spectral overlap between or among the different fluorophores.

* * * * *